United States Patent
Duan et al.

(10) Patent No.: US 8,592,395 B2
(45) Date of Patent: Nov. 26, 2013

(54) THERAPEUTIC COMPOUNDS

(75) Inventors: Maosheng Duan, Durham, NC (US); Wieslaw Mieczyslaw Kazmierski, Durham, NC (US); Matthew Tallant, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/386,731

(22) PCT Filed: Jul. 23, 2010

(86) PCT No.: PCT/US2010/042992
§ 371 (c)(1),
(2), (4) Date: Aug. 7, 2012

(87) PCT Pub. No.: WO2011/011652
PCT Pub. Date: Jan. 27, 2011

(65) Prior Publication Data
US 2012/0295877 A1  Nov. 22, 2012

Related U.S. Application Data

(60) Provisional application No. 61/228,193, filed on Jul. 24, 2009.

(51) Int. Cl.
| C07D 451/04 | (2006.01) |
| C07D 471/04 | (2006.01) |
| A61K 31/46 | (2006.01) |
| A61K 31/5377 | (2006.01) |
| A61K 31/675 | (2006.01) |
| A61P 1/00 | (2006.01) |
| A61P 11/06 | (2006.01) |
| A61P 13/12 | (2006.01) |
| A61P 17/00 | (2006.01) |
| A61P 17/02 | (2006.01) |
| A61P 19/04 | (2006.01) |
| A61P 25/00 | (2006.01) |
| A61P 25/28 | (2006.01) |
| A61P 29/00 | (2006.01) |
| A61P 31/18 | (2006.01) |
| A61P 31/20 | (2006.01) |
| A61P 35/00 | (2006.01) |
| A61P 37/06 | (2006.01) |
| A61P 37/08 | (2006.01) |
| C07F 9/6561 | (2006.01) |

(52) U.S. Cl.
USPC .......... 514/80; 514/233.2; 514/303; 514/304; 544/127; 546/23; 546/118; 546/126

(58) Field of Classification Search
None
See application file for complete search history.

(56) References Cited

FOREIGN PATENT DOCUMENTS

| WO | 99/04794 A1 | 2/1999 |
| WO | 2004/055011 A1 | 7/2004 |
| WO | 2005/007629 A1 | 1/2005 |

OTHER PUBLICATIONS

Armour, et al. The Discovery of Tropane-derived CCR5 Receptor Antagonists. Chem Biol. Drug. Des. 2006, vol. 67, pp. 305-308.
Silverman, The Organic Chemistry of Drug Design and Drug Action. Academic Press, Inc. New York, 1992, pp. 19-23.
Xiao-Qin, et al. Building three-dimensional structures of HIV-1 co-receptor CCR5 and its interaction with antagonist TAK779 by comparative molecular modeling. Acta Pharmacol. Sin. 2000, vol. 21(6), pp. 521-528.

*Primary Examiner* — Janet Andres
*Assistant Examiner* — Timothy R Rozof
(74) *Attorney, Agent, or Firm* — Karen L. Prus

(57) ABSTRACT

The present invention relates to compounds of Formula (I) and (Ia)

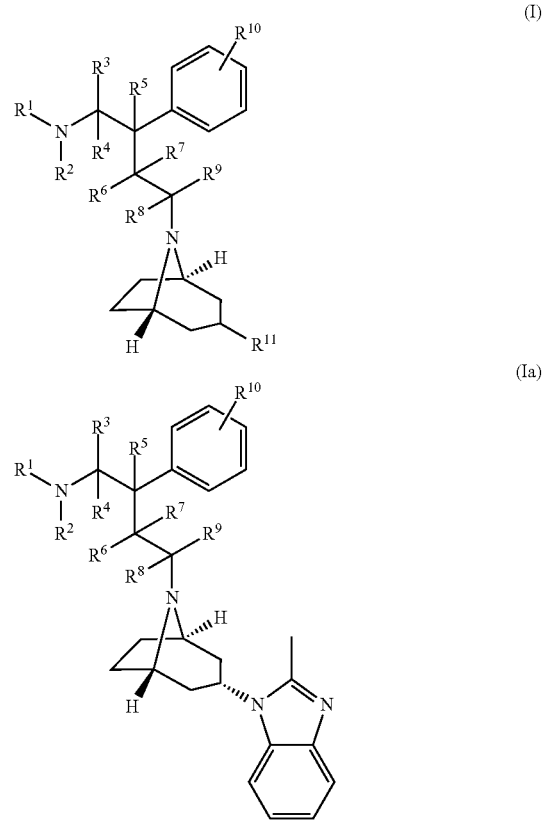

useful in the treatment of CCR5-related diseases and disorders, for example, the prevention or treatment of an HIV infection, and in the treatment of the resulting acquired immune deficiency syndrome (AIDS).

10 Claims, No Drawings

THERAPEUTIC COMPOUNDS

This application is a United States national stage of International Application No. PCT/US2010/042992 filed Jul. 23, 2010 which claims priority from U.S. Provisional No. 61/228,193 filed in the United States on Jul. 24, 2009 the contents of which are incorporated herein by reference

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are thought to be useful as therapeutic agents active against HIV.

We have now discovered compounds that are useful as a therapeutic agents in the treatment of HIV infection.

BRIEF DESCRIPTION OF THE INVENTION

The present invention features a compound of Formula (I)

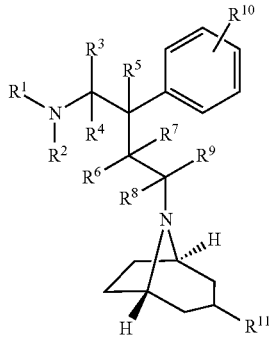

(I)

wherein:
$R^1$ is
(a) $S(O)_2R^{12}$ wherein $R^{12}$ is $C_{1-6}$alkyl; haloalkyl; heterocyclyl optionally substituted with oxo; aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen;
(b) $P(O)(OR^{15})_2$ wherein $R^{15}$ is $C_{1-6}$alkyl; or
(c) $C(O)R^{14}$;
$R^2$ is hydrogen or $C_{1-6}$alkyl;
$R^3$-$R^9$ is hydrogen, halogen or $C_{1-6}$alkyl;
$R^{10}$ is one or more substituents independently selected from the group consisting of hydrogen, halogen and $C_{1-6}$alkyl;
$R^{11}$ is heterocyclyl optionally substituted with one or more substituents independently selected from the group consisting of $C_{1-6}$alkyl and $C(O)R^{15}$;
or a pharmaceutically acceptable salt thereof.

Compounds of Formula (I) are useful in the inhibition of HIV replication, the prevention of infection by HIV, the treatment of infection by HIV and in the treatment of AIDS and/or ARC. The present invention further features methods of treating AIDS, methods of preventing infection by HIV, and methods of treating infection by HIV as monotherapy or in combination with other antivirals, anti-infectives, immunomodulators, antibiotics or vaccines. The present invention also features pharmaceutical compositions, comprising compounds of Formula (I) that are suitable for the prevention or treatment of CCR5-related diseases and conditions. The present invention further features processes for making the compounds of Formula (I).

DETAILED DESCRIPTION OF THE INVENTION

The present invention features a compound of Formula (I):

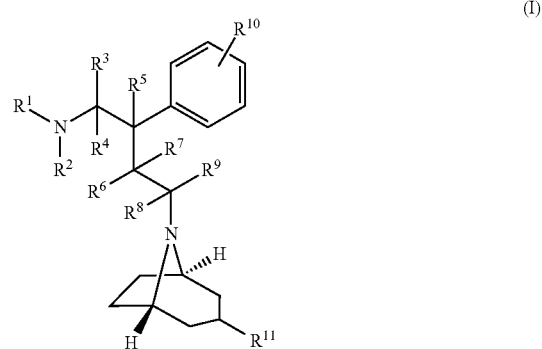

(I)

wherein:
$R^1$ is
(a) $S(O)_2R^{12}$ wherein $R^{12}$ is $C_{1-6}$alkyl; haloalkyl; heterocyclyl optionally substituted with oxo; aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen;
(b) $P(O)(OR^{15})_2$ wherein $R^{15}$ is $C_{1-6}$alkyl; or
(c) $C(O)R^{14}$;
$R^2$ is hydrogen or $C_{1-6}$alkyl;
$R^3$-$R^9$ is hydrogen, halogen or $C_{1-6}$alkyl;
$R^{10}$ is one or more substituents independently selected from the group consisting of hydrogen, halogen and $C_{1-6}$alkyl;
$R^{11}$ is heterocyclyl optionally substituted with one or more substituents independently selected from the group consisting of $C_{1-6}$alkyl and $C(O)R^{15}$;
or a pharmaceutically acceptable salt thereof.

The present invention features a compound of Formula (I) wherein:
$R^1$ is
(a) $S(O)_2R^{12}$ wherein $R^{12}$ is $C_{1-6}$alkyl; haloalkyl; heterocyclyl optionally substituted with oxo; aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen; or
(b) $P(O)(OR^{15})_2$ wherein $R^{15}$ is $C_{1-6}$alkyl;
$R^2$ is hydrogen or $C_{1-6}$alkyl;
$R^3$-$R^9$ is hydrogen;
$R^{10}$ is hydrogen;
$R^{11}$ is heterocyclyl optionally substituted with one or more substituents independently selected from the group consisting of $C_{1-6}$alkyl and $C(O)R^{15}$;
or a pharmaceutically acceptable salt thereof.

The present invention features a compound of Formula (I) wherein:
R¹ is
(a) S(O)₂R¹² wherein R¹² is aryl optionally substituted with CN or C(O)N(R¹³)₂ wherein R¹³ is hydrogen; or NR¹⁴ wherein R¹⁴ is C₃₋₆cycloalkyl optionally substituted with one or more halogen;
R² is hydrogen or C₁₋₆alkyl;
R³-R⁹ is hydrogen;
R¹⁰ is hydrogen;
R¹¹ is heterocyclyl optionally substituted with one or more substituents independently selected from the group consisting of C₁₋₆alkyl and C(O)R¹⁵;
or a pharmaceutically acceptable salt thereof.

The present invention features a compound of Formula (I) wherein R¹¹ is benzimidazolyl or triazolyl.

The invention also features a compound of Formula (Ia)

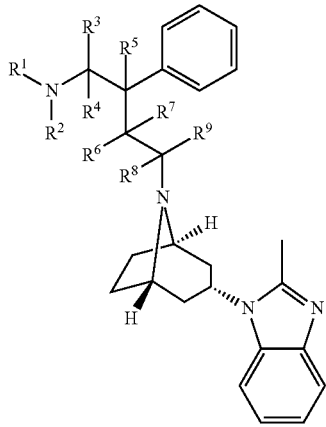

(Ia)

wherein:
R¹ is
(a) S(O)₂R¹² wherein R¹² is C₁₋₆alkyl; haloalkyl; heterocyclyl optionally substituted with oxo; aryl optionally substituted with CN or C(O)N(R¹³)₂ wherein R¹³ is hydrogen; or NR¹⁴ wherein R¹⁴ is C₃₋₆cycloalkyl optionally substituted with one or more halogen;
(b) P(O)(OR¹⁵)₂ wherein R¹⁵ is C₁₋₆alkyl; or
(c) C(O)R14;
R² is hydrogen or C₁₋₆alkyl;
R³-R⁹ is hydrogen, halogen or C₁₋₆alkyl;
or a pharmaceutically acceptable salt thereof.

The present invention features a compound of Formula (Ia) wherein
R¹ is
(a) S(O)₂R¹² wherein R¹² is C₁₋₆alkyl; haloalkyl; heterocyclyl optionally substituted with oxo; aryl optionally substituted with CN or C(O)N(R¹³)₂ wherein R¹³ is hydrogen; or NR¹⁴ wherein R¹⁴ is C₃₋₆cycloalkyl optionally substituted with one or more halogen; or
(b) P(O)(OR¹⁵)₂ wherein R¹⁵ is C₁₋₆alkyl;
R² is hydrogen or C₁₋₆alkyl;
R³-R⁹ is hydrogen;
or a pharmaceutically acceptable salt thereof.

The present invention features a compound of formula (Ia) wherein
R¹ is
(a) S(O)₂R¹² wherein R¹² is aryl optionally substituted with CN or C(O)N(R¹³)₂ wherein R¹³ is hydrogen; or NR¹⁴ wherein R¹⁴ is C₃₋₆cycloalkyl optionally substituted with one or more halogen;

R² is hydrogen or C₁₋₆alkyl;
R³-R⁹ is hydrogen;
or a pharmaceutically acceptable salt thereof.

The present invention features a compound of formula (I) or (Ia) as described above wherein R⁵ is hydrogen, halogen, or C₁₋₆alkyl.

The present invention features a compound of formula (I) or (Ia) as described above wherein R⁵ is C₁₋₆alkyl.

The present invention features a compound of formula (I) or (Ia) as described above wherein R⁵ is methyl.

The present invention features a compound of formula (I) or (Ia) as described above wherein R² is C₁₋₆alkyl.

The present invention features a compound of formula (I) or (Ia) as described above wherein R² is methyl.

The present invention features a compound selected from the group consisting of:
N-{4-[(1R,5S)-3-(2-methyl-1H-benzimidazol-1-yl)-8-azabicyclo[3.2.1]oct-8-yl]-2-phenylbutyl};
N-methyl-N-{4-[(1R,5S)-3-(2-methyl-1H-benzimidazol-1-yl)-8-azabicyclo[3.2.1]oct-8-yl]-2-phenylbutyl}benzenesulfonamide;
3-cyano-N-{4-[(1R,5S)-3-(2-methyl-1H-benzimidazol-1-yl)-8-azabicyclo[3.2.1]oct-8-yl]-2-phenylbutyl}benzenesulfonamide;
4-cyano-N-{4-[(1R,5S)-3-(2-methyl-1H-benzimidazol-1-yl)-8-azabicyclo[3.2.1]oct-8-yl]-2-phenylbutyl}benzenesulfonamide;
N-{4-[(1R,5S)-3-(2-methyl-1H-benzimidazol-1-yl)-8-azabicyclo[3.2.1]oct-8-yl]-2-phenylbutyl}methanesulfonamide;
3-[({4-[(1R,5S)-3-(2-methyl-1H-benzimidazol-1-yl)-8-azabicyclo[3.2.1]oct-8-yl]-2-phenylbutyl}amino)sulfonyl]benzamide;
N-{4-[(1R,5S)-3-(2-methyl-1H-benzimidazol-1-yl)-8-azabicyclo[3.2.1]oct-8-yl]-2-phenylbutyl}-2-oxo-2,3-dihydro-1,3-benzoxazole-6-sulfonamide;
4-[({4-[(1R,5S)-3-(2-methyl-1H-benzimidazol-1-yl)-8-azabicyclo[3.2.1]oct-8-yl]-2-phenylbutyl}amino)sulfonyl]benzamide;
dimethyl{4-[(1R,5S)-3-(2-methyl-1H-benzimidazol-1-yl)-8-azabicyclo[3.2.1]oct-8-yl]-2-phenylbutyl}amidophosphate;
2,2,2-trifluoro-N-{4-[(1R,5S)-3-(2-methyl-1H-benzimidazol-1-yl)-8-azabicyclo[3.2.1]oct-8-yl]-2-phenylbutyl}ethanesulfonamide;
N-{4-[(1R,5S)-3-(2-methyl-3H-imidazo[4,5-c]pyridin-3-yl)-8-azabicyclo[3.2.1]oct-8-yl]-2-phenylbutyl}benzenesulfonamide;
N-{4-[(1R,5S)-3-(2-methyl-1H-benzimidazol-1-yl)-8-azabicyclo[3.2.1]oct-8-yl]-2-phenylbutyl}-4-morpholinesulfonamide;
N-{4-[(1R,5S)-3-(5-acetyl-2-methyl-4,5,6,7-tetrahydro-3H-imidazo[4,5-c]pyridin-3-yl)-8-azabicyclo[3.2.1]oct-8-yl]-2-phenylbutyl}benzenesulfonamide;
N-cyclobutyl-N'-{4-[(1R,5S)-3-(2-methyl-1H-benzimidazol-1-yl)-8-azabicyclo[3.2.1]oct-8-yl]-2-phenylbutyl}sulfamide;
N-(4,4-difluorocyclohexyl)-N'-{4-[(1R,5S)-3-(2-methyl-1H-benzimidazol-1-yl)-8-azabicyclo[3.2.1]oct-8-yl]-2-phenylbutyl}sulfamide;
4,4-difluoro-N-(4-{(1R,5S)-3-[3-methyl-5-(1-methylethyl)-4H-1,2,4-triazol-4-yl]-8-azabicyclo[3.2.1]oct-8-yl}-2-phenylbutyl)cyclohexanecarboxamide;
N-(4-{(1R,5S)-3-[3-methyl-5-(1-methylethyl)-4H-1,2,4-triazol-4-yl]-8-azabicyclo[3.2.1]oct-8-yl}-2-phenylbutyl)benzenesulfonamide;

3,3-difluoro-N-(4-{(1R,5S)-3-[3-methyl-5-(1-methylethyl)-4H-1,2,4-triazol-4-yl]-8-azabicyclo[3.2.1]oct-8-yl}-2-phenylbutyl)cyclobutanecarboxamide;

N-{2-methyl-4-[(1R,5S)-3-(2-methyl-1H-benzimidazol-1-yl)-8-azabicyclo[3.2.1]oct-8-yl]-2-phenylbutyl}benzenesulfonamide;

N-methyl-N-{2-methyl-4-[(1R,5S)-3-(2-methyl-1H-benzimidazol-1-yl)-8-azabicyclo[3.2.1]oct-8-yl]-2-phenylbutyl}benzenesulfonamide;

4,4-difluoro-N-{2-methyl-4-[(1R,5S)-3-(2-methyl-1H-benzimidazol-1-yl)-8-azabicyclo[3.2.1]oct-8-yl]-2-phenylbutyl}cyclohexanecarboxamide;

4,4-difluoro-N-methyl-N-{2-methyl-4-[(1R,5S)-3-(2-methyl-1H-benzimidazol-1-yl)-8-azabicyclo[3.2.1]oct-8-yl]-2-phenylbutyl}cyclohexanecarboxamide;

4,4-difluoro-N-(2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)cyclohexanecarboxamide;

N-(2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)benzenesulfonamide;

N-methyl-N-{(2S)-2-methyl-4-[(1R,5S)-3-(2-methyl-1H-benzimidazol-1-yl)-8-azabicyclo[3.2.1]oct-8-yl]-2-phenylbutyl}benzenesulfonamide;

and pharmaceutically acceptable salts thereof.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl" refers to a saturated or partially saturated carbocyclic ring composed of 3-6 carbons in any chemically stable configuration. Examples of suitable carbocyclic groups include cyclopropyl, cyclobutyl, cyclopentyl, cyclohexyl, and cyclohexenyl.

The term "aryl" alone or in combination with any other term, refers to a carbocyclic aromatic moiety (such as phenyl or naphthyl) containing the specified number of carbon atoms, preferably from 6-14 carbon atoms, and more preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "heterocycle," "heterocyclic," and "heterocyclyl" as used herein, refer to a 3- to 7-membered monocyclic heterocyclic ring or 8- to 11-membered bicyclic heterocyclic ring system any ring of which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and the nitrogen atom may optionally be quaternized, and including any bicyclic group in which any of the above-defined heterocyclic rings is fused to a benzene ring. The heterocyclic ring may be attached at any carbon or heteroatom, provided that the attachment results in the creation of a stable structure. Preferred heterocycles include 5-7 membered monocyclic heterocycles and 8-10 membered bicyclic heterocycles. When the heterocyclic ring has substituents, it is understood that the substituents may be attached to any atom in the ring, whether a heteroatom or a carbon atom, provided that a stable chemical structure results.

"Heteroaromatics" or "heteroaryl" are included within the heterocycles as defined above and generally refers to a heterocycle in which the ring system is an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls. Also included within the scope of the term "heterocycle, "heterocyclic" or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle, "heterocyclic" or "heterocyclyl" also included each possible positional isomer of a heterocyclic radical, such as in 1-indolinyl, 2-indolinyl, 3-indolinyl. Examples of heterocycles include imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, benzimidazolyl, thiamorpholinyl sulfone, oxazolyl, oxadiazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroatom" means nitrogen, oxygen, or sulfur and includes any oxidized form of nitrogen, such as $N(O)\{N^+\!-\!O^-\}$ and sulfur such as $S(O)$ and $S(O)_2$, and the quaternized form of any basic nitrogen.

Compounds of Formula (I) and IIa) are useful in the inhibition of HIV replication, the prevention of infection by HIV, the treatment of infection by HIV and in the treatment of AIDS and/or ARC. The present invention further features methods of treating AIDS, methods of preventing infection by HIV, and methods of treating infection by HIV as monotherapy or in combination with other antivirals, anti-infectives, immunomodulators, antibiotics or vaccines. The present invention also features pharmaceutical compositions, comprising a compound of Formula (I) or (Ia) that are suitable for the prevention or treatment of CCR5-related diseases and conditions. The present invention further features processes for making a compound of Formula (I) or (Ia).

The term "pharmaceutically effective amount" refers to an amount of a compound of the invention that is effective in treating a CCR5-related disease, for example a virus infection, for example an HIV infection, in a patient either as monotherapy or in combination with other agents.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

The term "pharmaceutically acceptable carrier" refers to a carrier that may be administered to a patient, together with a compound of Formula (I) or (Ia), and which does not destroy the pharmacological activity thereof and is nontoxic when administered in doses sufficient to deliver a therapeutic amount of the therapeutic agent.

Pharmaceutically acceptable salts of compounds of Formula (I) or (Ia) include those derived from pharmaceutically acceptable inorganic and organic acids and bases. Examples of suitable acids include hydrochloric, hydrobromic, sulfuric, nitric, perchloric, fumaric, glutamic, maleic, mandelic, phosphoric, glycollic, lactic, salicyclic, succinic, toluene-p-sulfonic, tartaric, acetic, citric, orotic, toluenesulfonic, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining a compound of Formula (I) or (Ia) or its pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$ alkyl group).

Salts of a compound of Formula (I) or (Ia) may be made by methods known to a person skilled in the art. For example, treatment of a compound of Formula (I) or (Ia) with an appropriate base or acid in an appropriate solvent will yield the corresponding salt.

The present invention features a compound of Formula (I) or (Ia) for use in medical therapy, for example for the treatment or prophylaxis of viral infections such as an HIV infections and associated conditions. Reference herein to treatment may extend to prophylaxis as well as the treatment of established infections, symptoms, and associated clinical conditions such as AIDS related complex (ARC), Kaposi's sarcoma, and AIDS dementia.

The present invention features use of a compound of Formula (I) or (Ia) in the manufacture of a medicament for the treatment or prophylaxis of a CCR5-related disease or condition, for example, a viral infection, for example, an HIV infection.

According to another aspect, the present invention provides a method for the treatment or prevention of the symptoms or effects of a viral infection in an infected animal, for example, a mammal including a human, which comprises treating said animal with a pharmaceutically effective amount of a compound Formula (I) or (Ia). According to one aspect of the invention, the viral infection is a retroviral infection, in particular an HIV infection.

A compound of Formula (I) or (Ia) according to the invention may also be used in adjuvant therapy in the treatment of HIV infections or HIV-associated symptoms or effects, for example Kaposi's sarcoma.

A compound of Formula (I) or (Ia) may also be used in the prevention or treatment of other CCR5-related diseases and conditions, including neuropathic pain, multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, human papilloma virus infection, prostate cancer, wound healing, amyotrophic lateral sclerosis, immune mediated disorders.

The present invention further provides a method for the treatment of a clinical condition in an animal, for example, a mammal including a human which clinical condition includes those which have been discussed hereinbefore, which comprises treating said animal with a pharmaceutically effective amount of a compound of Formula (I). The present invention also includes a method for the treatment or prophylaxis of any of the aforementioned diseases or conditions. In yet a further aspect, the present invention provides the use of a compound of Formula (I) or (Ia) in the manufacture of a medicament for the treatment or prophylaxis of any of the above mentioned viral infections or conditions.

A compound Formula (I) or (Ia) or a pharmaceutically acceptable salt thereof may be employed in combination with other therapeutic agents for the treatment of the above infections or conditions. Combination therapies according to the present invention comprise the administration of a compound of Formula (I) or (Ia) or a pharmaceutically acceptable salt thereof and another pharmaceutically active agent. The active ingredient(s) and pharmaceutically active agents may be administered simultaneously in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include agents that are effective for the treatment of viral infections or associated conditions. Among these agents are acyclic nucleosides, for example acyclovir, valaciclovir, famciclovir, ganciclovir, and penciclovir, acyclic nucleoside phosphonates, for example (S)-1-(3-hydroxy-2-phosphonyl-methoxypropyl)cytosine (HPMPC), [[[2-(6-amino-9H-purin-9-yl)ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), and (R)[[2-(6-Amino-9H-purin-9-yl)-1-methylethoxy]methyl]phosphonic acid bis-(isopropoxycarbonyloxymethyl)ester (bis-POC-PMPA), nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), (−)-cis-4-[2-amino-6-(cyclopropylamino)-9H-purin-9-yl]-2-cyclopentene-1-methanol (abacavir), and ribavirin, protease inhibitors, for example indinavir, ritonavir, nelfinavir, amprenavir, saquinavir, fosamprenavir, lopinavir, tipranavir, interferons such as α-interferon, immunomodulators such as interleukin II or thymosin, granulocyte macrophage colony stimulating factors, erythropoetin, soluble $CD_4$ and genetically engineered derivatives thereof, non-nucleoside reverse transcriptase inhibitors (NNRTIs), for example nevirapine (BI-RG-587), alpha-((2-acetyl-5-methylphenyl)amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (S)-6-chloro-4-(cyclopropylethynyl)-1,4-dihydro-4-(trifluoromethyl)-2H-3,1-benzoxazin-2-one (efavirenz, DMP 266), rilpivirine, integrase inhibitors, or fusion inhibitors, for example T-20 and T-1249.

The present invention further includes the use of a compound Formula (I) or (Ia) in the manufacture of a medicament for simultaneous or sequential administration with at least another therapeutic agent, such as those defined hereinbefore.

A compound of Formula (I) or (Ia) may be administered with an agent known to inhibit or reduce the metabolism of compounds, for example ritonavir. Accordingly, the present invention features a method for the treatment or prophylaxis of a disease as hereinbefore described by administration of a compound of Formula (I) or (Ia) in combination with a metabolic inhibitor. Such combination may be administered simultaneously or sequentially.

In general a suitable dose for each of the above-mentioned conditions will be in the range of, for example, 0.01 to 250 mg per kilogram body weight of the recipient (e.g. a human) per day, in the range of 0.1 to 100 mg per kilogram body weight per day, in the range 0.5 to 30 mg per kilogram body weight per day or in the range 1.0 to 20 mg per kilogram body weight per day. Unless otherwise indicated, all weights of active ingredient are calculated as the parent compound of Formula (I) or (Ia); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, 20 to 500 mg, or 50 to 400 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in Pharmaceutical Research 3 (6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

The following examples are intended for illustration only and are not intended to limit the scope of the invention in any way.

Example 1

N-{4-[(1R,5S)-3-(2-methyl-1H-benzimidazol-1-yl)-8-azabicyclo[3.2.1]oct-8-yl]-2-phenylbutyl}

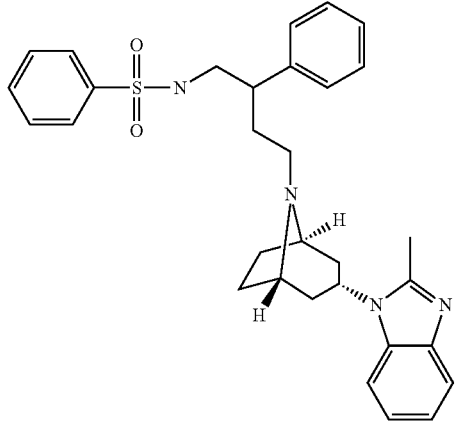 [SMILES: Cc1nc2ccccc2n1[C@H]1C[C@H]2CC[C@@H](C1)N2CCC(CNS(=O)(=O)c1ccccc1)c1ccccc1]

To a solution of intermediate 6 (105 mg, 0.27 mmol) in CH$_2$Cl$_2$ (3.0 mL) was added diisopropylethylamine (0.12 mL, 0.68 mmol) followed by phenylsulfonyl chloride (0.045 mL, 0.34 mmol) and the solution stirred at room temperature under nitrogen atmosphere for 18 h. The reaction was concentrated in vacuo and purified by silica gel chromatography eluting with 0-5% CH$_2$Cl$_2$/MeOH to give the title compound (80 mg, 56% yield) as a white solid.

$^1$H NMR (DMSO-d$_6$, 400 MHz) δ 7.70-7.78 (m, 3H), 7.53-7.64 (m, 3H), 7.49 (d, J=7.33 Hz, 1H), 7.38 (d, J=7.33 Hz, 1H), 7.25-7.31 (m, 2H), 7.16-7.22 (m, 3H), 7.07-7.16 (m, 2H), 4.54-4.67 (m, 1H), 3.21-3.29 (m, 2H), 2.80-3.00 (m, 3H), 2.51 (s, 3H), 2.29-2.44 (m, 2H), 1.85-2.01 (m, 5H), 1.79 (t, J=12.28 Hz, 2H), 1.52-1.68 (m, 3H). HRMS: (M+H)$^+$ calcd for C$_{31}$H$_{36}$N$_4$O$_2$S+H, 529.2632. found, 529.2632.

Preparation of Intermediate 6

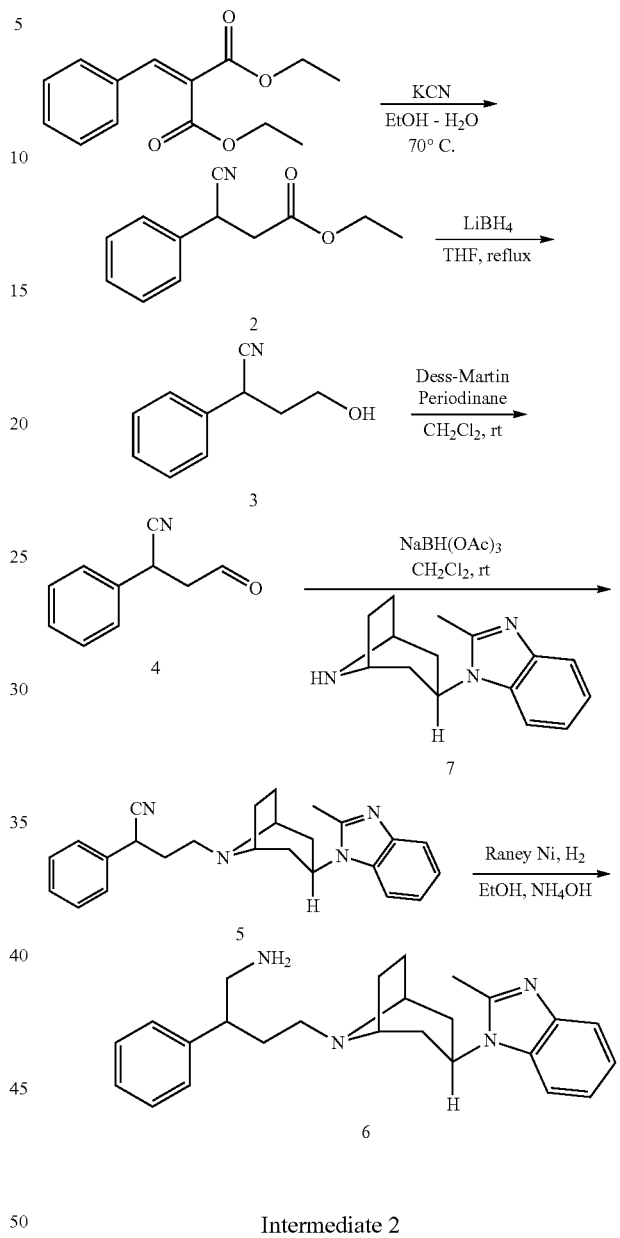

Intermediate 2

Ethyl 3-cyano-3-phenylpropanoate

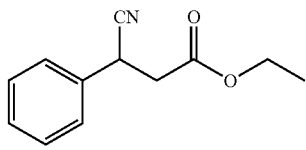

To a solution of diethyl(phenylmethylidene)propanedioate (15.0 g, 60.4 mmol) in ethanol (150 mL) and water (18 mL) was added potassium cyanide (4.3 g, 66.4 mmol) and the solution heated to 70° C. for 18 h. The reaction was cooled to room temperature, diluted with diethyl ether (900 mL), washed with water (900 mL) followed by brine and the organic layer dried (MgSO₄) and concentrated in vacuo to give 2 (9.01 g, 73% yield) as a white solid.

1H NMR (400 MHz, DMSO-d₆) d ppm 7.27-7.49 (m, 5H) 4.50 (dd, J=8.61, 6.05 Hz, 1H) 4.06 (q, J=7.09 Hz, 2H) 3.03-3.17 (m, 1H) 2.85-3.01 (m, 1H) 1.14 (t, J=7.15 Hz, 3H).

ES-LCMS: m/z 204.13 (M+H)⁺.

Intermediate 3

4-hydroxy-2-phenylbutanenitrile

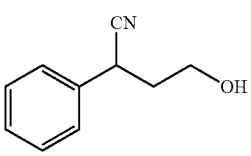 [SMILES: N#CC(CCO)c1ccccc1]

To a solution of ethyl 3-cyano-3-phenylpropanoate 2 (8.0 g, 39.4 mmol) in dry THF (200 mL) was added LiBH₄ as a 2M solution in THF (40 mL) and the solution heated to 65° C. under nitrogen atmosphere for 2 h. The reaction was cooled to rt, poured into saturated NaHCO₃ (800 mL) and stirred for 10 min and extracted with EtOAc (2×600 mL). The organic layers were combined and dried (MgSO₄) and concentrated in vacuo. The residue was purified by silica gel chromatography eluting with 20-75% hexanes/ethyl acetate to give 3 (3.72 g, 59% yield) as a clear oil.

1H NMR (400 MHz, DMSO-d₆) d ppm 7.23-7.44 (m, 5H) 4.75 (t, J=4.94 Hz, 1H) 4.19 (dd, J=8.97, 6.59 Hz, 1H) 3.33-3.55 (m, 2H) 1.78-2.12 (m, 2H). ES-LCMS: m/z 162.12 (M+H)⁺.

Intermediate 4

4-oxo-2-phenylbutanenitrile

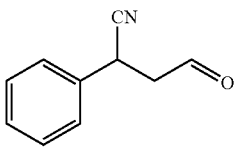 [SMILES: N#CC(CC=O)c1ccccc1]

To a solution of 4-hydroxy-2-phenylbutanenitrile 3 (2.0 g, 12.4 mmol) in dry CH₂Cl₂ (100 mL) was added Dess-Martin Periodinane (10.5 g, 24.8 mmol) and the solution stirred at room temperature under nitrogen atmosphere for 1 h. The reaction was poured into an aqueous solution of Na₂S₂O₃ (350 mL) and saturated NaHCO₃ (200 mL) and stirred for 10 minutes. The solution was extracted with CH₂Cl₂ (2×200 mL), the organic layers combined and dried (MgSO₄) and concentrated in vacuo. The residue was purified by silica gel chromatography eluting with 20-75% hexanes/ethyl acetate to give 4 (1.75 g, 89% yield) as a pale yellow oil.

1H NMR (400 MHz, DMSO-d₆) d ppm 9.63 (s, 1H) 7.24-7.53 (m, 5H) 4.54 (dd, J=8.71, 5.59 Hz, 1H) 3.15 (d, J=5.68 Hz, 1H) 3.10 (d, J=5.50 Hz, 1H). ES-LCMS: m/z 158.19 (M-H)⁻.

Intermediate 5

4-[3-(2-methyl-1H-benzimidazol-1-yl)-8-azabicyclo [3.2.1]oct-8-yl]-2-phenylbutanenitrile

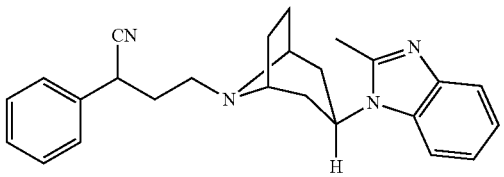 [SMILES: Cc1nc2ccccc2n1C1CC2CCC(C1)N2CCC(C#N)c1ccccc1]

To a solution of 4-oxo-2-phenylbutanenitrile 4 (375 mg, 2.3 mmol) in dry CH₂Cl₂ (20 mL), was added 1-(8-azabicyclo [3.2.1]oct-3-yl)-2-methyl-1H-benzimidazole 7 (660 mg, 2.6 mmol) prepared as previously described in WO 2000/038680 A1 followed by the addition of NaBH(OAc)₃ (1.0 g, 4.6 mmol) and the solution stirred at room temperature under an atmosphere of nitrogen for 18 h. The reaction was poured into aqueous K₂CO₃ solution (50 mL), extracted with CH₂Cl₂ (2×50 mL). The organic layers were combined and dried (MgSO₄) and concentrated in vacuo. The residue was purified by silica gel chromatography eluting with 0-10% ethyl acetate/methanol to afford 5 (618 mg, 70% yield) as an off-white solid.

1H NMR (400 MHz, DMSO-d₆) d ppm 7.35-7.51 (m, 6H) 7.26-7.35 (m, 1H) 7.00-7.16 (m, 2H) 4.67-4.83 (m, 1H) 4.36 (dd, J=8.33, 5.59 Hz, 1H) 3.32 (br. s., 2H) 2.50 (s, 3H) 2.24 (t, J=6.23 Hz, 2H) 1.98-2.11 (m, 3H) 1.87-1.98 (m, 1H) 1.82 (t, J=12.45 Hz, 2H) 1.59-1.75 (m, 2H). ES-LCMS: m/z 385.35 (M+H)⁺.

1-(8-Azabicyclo[3.2.1]oct-3-yl)-2-methyl-1H-benzimidazole 7 may be made according to procedures disclosed in WO 2004/054974 or Journal of Medicinal Chemistry (2008), 51(20), 6538-6546.

Intermediate 6

4-[3-(2-methyl-1H-benzimidazol-1-yl)-8-azabicyclo [3.2.1]oct-8-yl]-2-phenyl-1-butanamine

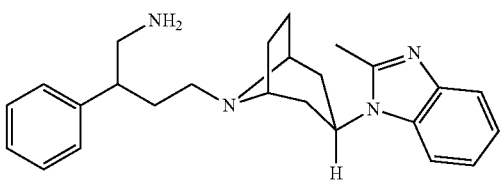 [SMILES: Cc1nc2ccccc2n1C1CC2CCC(C1)N2CCC(CN)c1ccccc1]

To a solution of 4-[3-(2-methyl-1H-benzimidazol-1-yl)-8-azabicyclo[3.2.1]oct-8-yl]-2-phenylbutanenitrile 5 (610 mg, 1.6 mmol) in absolute ethanol (20 mL) was added concentrated aqueous ammonia (3.5 mL) followed by a spatula of Raney Nickel and the mixture hydrogenated on a Fischer-Porter apparatus at 50 psi for 18 h whereupon the reaction was found to be complete by TLC. The reaction was filtered through celite and concentrated in vacuo to give 6 (613 mg, 99% yield) as a white solid which was used in subsequent reactions without further purification.

1H NMR (400 MHz, DMSO-d₆) d ppm 7.47 (d, J=7.15 Hz, 1H) 7.38 (d, J=7.33 Hz, 1H) 7.29 (d, J=7.33 Hz, 2H) 7.15-7.26 (m, 3H) 7.10 (dd, J=16.04, 1.19 Hz, 2H) 4.49-4.68 (m, 1H) 2.73 (br. s., 2H) 2.56-2.67 (m, 1H) 2.25-2.42 (m, 4H) 1.86-2.15 (m, 8H) 1.71-1.86 (m, 3H) 1.54-1.71 (m, 4H). ES-LCMS m/z 389.34 (M+H)+.

Example 2

N-methyl-N-{4-[(1R,5S)-3-(2-methyl-1H-benzimidazol-1-yl)-8-azabicyclo[3.2.1]oct-8-yl]-2-phenylbutyl}benzenesulfonamide

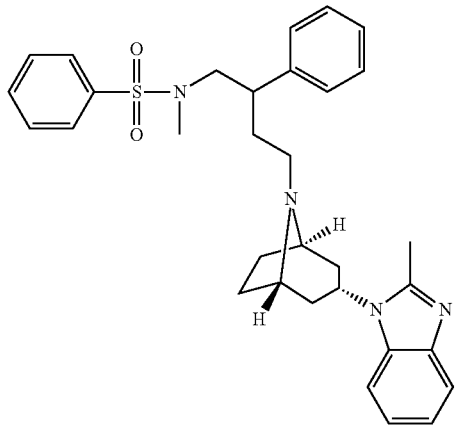 [SMILES: Cc1nc2ccccc2n1[C@H]1C[C@H]2CC[C@@H](C1)N2CCC(CN(C)S(=O)(=O)c1ccccc1)c1ccccc1]

To a solution of intermediate 14 (90 mg, 0.28 mmol) in dry CH₂Cl₂ (3 mL), was added 1-(8-azabicyclo[3.2.1]oct-3-yl)-2-methyl-1H-benzimidazole 7 (660 mg, 2.6 mmol) followed by the addition of NaBH(OAc)₃ (120 mg, 0.56 mmol) and the solution stirred at room temperature under an atmosphere of nitrogen for 18 h. The reaction was poured into aqueous saturated NaHCO₃ and extracted with CH₂Cl₂. The organic layers were combined and dried (MgSO₄) and concentrated in vacuo. The residue was purified by silica gel chromatography eluting with 0-10% ethyl acetate/methanol to afford the title compound (95 mg, 63% yield) as a white solid.

¹H NMR (DMSO-d₆, 400 MHz) δ 7.72 (d, J=7.51 Hz, 2H), 7.64-7.69 (m, 1H), 7.59 (t, J=7.92 Hz, 2H), 7.49 (d, J=7.94 Hz, 1H), 7.38 (d, J=7.91 Hz, 1H), 7.19-7.34 (m, 6H), 7.06-7.15 (m, 2H), 4.56-4.67 (m, 1H), 3.19-3.29 (m, 3H), 3.01-3.16 (m, 3H), 2.58 (s, 3H), 2.30-2.44 (m, 3H), 2.04 (t, J=6.97 Hz, 2H), 1.93-1.99 (m, 3H), 1.76-1.87 (m, 3H), 1.59-1.70 (m, 4H). HRMS: (M+H)+ calcd for C₃₂H₃₈N₄O₂S+H, 543.2788. found, 543.2789.

Preparation of Intermediate 14

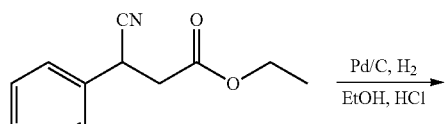

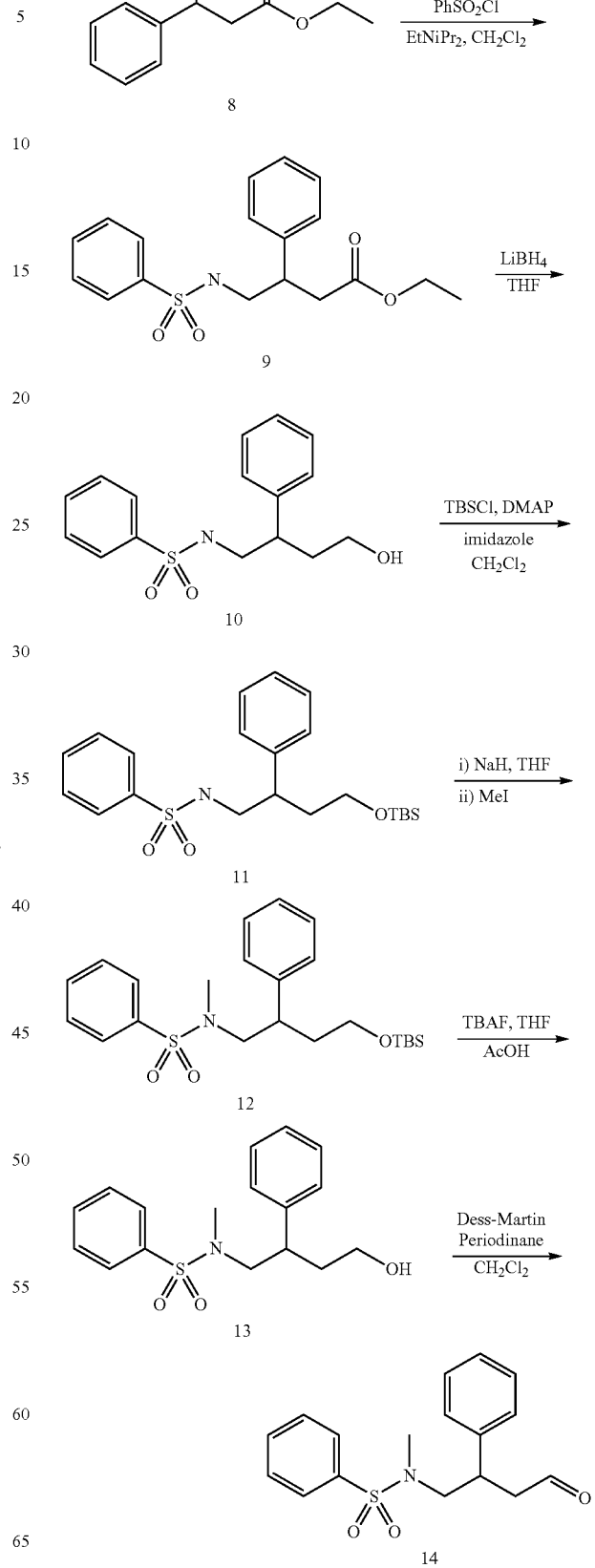

Intermediate 8

Ethyl 4-amino-3-phenylbutanoate hydrochloride

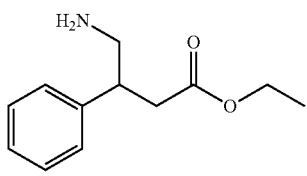

To a solution of ethyl 3-cyano-3-phenylpropanoate 2 (9.27 g, 45.6 mmol) in ethanol (70 mL) was added concentrated hydrochloric acid (2.4 mL) followed by 10% palladium on carbon (1.0 g) and the reaction hydrogenated at 80 psi for 18 h. The mixture was filtered through celite and concentrated in vacuo. The residue was triturated in ether and filtered to give 2 (4.97 g in 2 crops, 45%) as a white solid.

1H NMR (400 MHz, DMSO-$d_6$) d ppm 7.85 (br. s., 3H) 7.16-7.38 (m, 5H) 3.91 (qd, J=7.09, 2.75 Hz, 2H) 3.05-3.17 (m, 1H) 2.95-3.04 (m, 1H) 2.88 (dd, J=15.95, 5.50 Hz, 1H) 2.61 (dd, J=16.04, 9.62 Hz, 1H) 1.01 (t, J=7.15 Hz, 3H). ES-LCMS: m/z 208.33 $(M+H)^+$.

Intermediate 9

Ethyl 3-phenyl-4-[(phenylsulfonyl)amino]butanoate

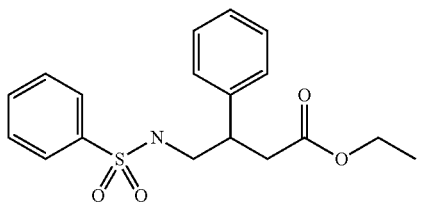 [SMILES: CCOC(=O)CC(CNS(=O)(=O)c1ccccc1)c1ccccc1]

To a suspension of ethyl 4-amino-3-phenylbutanoate hydrochloride 8 (3.0 g, 12.3 mmol) in dry $CH_2Cl_2$ (60 mL) was added phenylsulfonyl chloride (1.6 mL, 12.3 mmol) followed by diisopropylethylamine (6.5 mL, 36.9 mmol) and the solution stirred at room temperature under a nitrogen atmosphere for 18 h. The reaction was poured into $CH_2Cl_2$ and washed with 0.1 N HCl and the organic layer dried ($MgSO_4$) and concentrated in vacuo. The residue was purified by silica gel chromatography eluting with 10-60% hexanes/ethyl acetate to give 9 (3.94 g, 92%).

1H NMR (400 MHz, DMSO-$d_6$) d ppm 7.71 (d, 3H) 7.51-7.64 (m, 3H) 7.21-7.29 (m, 2H) 7.10-7.21 (m, 3H) 3.87 (qd, J=7.09, 2.93 Hz, 2H) 3.06-3.18 (m, 1H) 2.90 (br. s., 2H) 2.74 (dd, J=15.76, 5.50 Hz, 1H) 0.99 (t, J=7.15 Hz, 3H) ES-LCMS: m/z 348.22 $(M+H)^+$.

Intermediate 10

N-(4-hydroxy-2-phenylbutyl)benzenesulfonamide

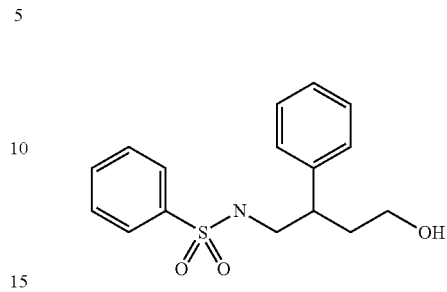

To a solution of ethyl 3-phenyl-4-[(phenylsulfonyl)amino]butanoate 9 (3.94 g, 11.3 mmol) in dry THF (100 mL) was added lithium borohydride as a 2M solution in THF (11.3 mL) and the reaction heated to 65° C. under a nitrogen atmosphere for 2 h. The reaction was cooled to room temperature and poured into aqueous pH 8 buffer (400 mL) and stirred for 10 min. The aqueous layer was extracted with ethyl acetate and the organic layer dried ($MgSO_4$) and concentrated in vacuo to give 10 in quantitative yield as a clear oil.

1H NMR (400 MHz, DMSO-$d_6$) d ppm 7.69 (d, J=7.33 Hz, 2H) 7.44-7.62 (m, 4H) 7.18-7.29 (m, 2H) 7.11-7.18 (m, 1H) 7.08 (d, J=7.14 Hz, 2H) 4.31 (t, J=4.94 Hz, 1H) 3.10-3.20 (m, 1H) 3.00-3.10 (m, 1H) 2.84 (t, J=6.13 Hz, 2H) 2.69-2.81 (m, 1H) 1.74-1.87 (m, 1H) 1.42-1.59 (m, 1H). ES-LCMS: m/z 306.13 $(M+H)^+$.

Intermediate 11

N-(4-{[(1,1-dimethylethyl)(dimethyl)silyl]oxy}-2-phenylbutyl)benzenesulfonamide

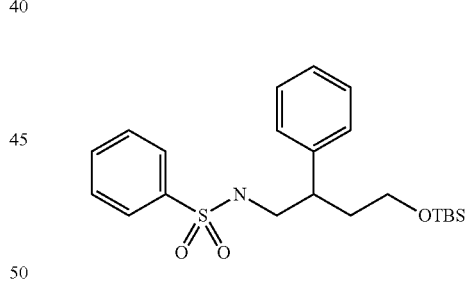

To a solution of N-(4-hydroxy-2-phenylbutyl)benzenesulfonamide 10 (3.45 g, 11.3 mmol) in dry $CH_2Cl_2$ (70 mL) was added imidazole (1.92 g, 28.2 mmol), 4-dimethylaminopyridine (160 mg, 1.3 mmol) and tert-butyldimethylsilyl chloride (2.21 g, 14.7 mmol) and the reaction stirred at room temperature under an atmosphere of nitrogen for 20 min. The reaction was poured into $CH_2Cl_2$ and washed sequentially with aqueous $K_2CO_3$ and water. The organic layer was dried ($MgSO_4$) and concentrated in vacuo. The residue was purified by silical gel chromatography eluting with 5-50% hexanes/ethyl acetate to give 11 (4.17 g, 88%).

1H NMR (400 MHz, DMSO-$d_6$) d ppm 7.73 (d, J=7.02 Hz, 2H) 7.48-7.68 (m, 4H) 7.26 (d, J=7.62 Hz, 2H) 7.15-7.22 (m, 1H) 7.12 (d, J=7.02 Hz, 2H) 3.34-3.44 (m, 1H) 3.18-3.29 (m, 1H) 2.90 (br. s., 2H) 2.76-2.86 (m, 1H) 1.82-1.95 (m, 1H)

1.54-1.66 (m, 1H) 0.80 (s, 9H)-0.10 (d, J=5.82 Hz, 6H). ES-LCMS: 420.15 m/z (M+H)+.

Intermediate 12

N-(4-{[(1,1-dimethylethyl)(dimethyl)silyl]oxy}-2-phenylbutyl)-N-methylbenzenesulfonamide

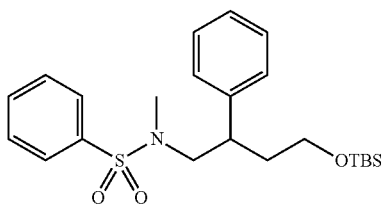 [SMILES: CN(CC(CCO[Si](C)(C)C(C)(C)C)c1ccccc1)S(=O)(=O)c1ccccc1]

To a solution of N-(4-{[(1,1-dimethylethyl)(dimethyl)silyl]oxy}-2-phenylbutyl)benzenesulfonamide 11 (419 mg, 1.0 mmol) in dry THF (10 mL) was added sodium hydride (48 mg, 1.2 mmol) as a 60% suspension in mineral oil and the solution stirred at room temperature for 1 h under an atmosphere of nitrogen. Methyl iodide (0.25 mL, 4.0 mmol) was added and the reaction stirred at room temperature for 2.5 h. Saturated NaHCO$_3$ was added and the reaction stirred for 10 min. The reaction was partitioned between ethyl acetate and water, the aqueous layer was separated and the organic layer washed with brine and dried (MgSO$_4$) and concentrated in vacuo to give 12 in quantitative yield as a yellow oil.

1H NMR (400 MHz, DMSO-d$_6$) d ppm 7.62-7.74 (m, 3H) 7.53-7.62 (m, 2H) 7.25-7.34 (m, 2H) 7.14-7.24 (m, 3H) 3.38-3.50 (m, 2H) 3.12-3.23 (m, 1H) 2.95-3.08 (m, 2H) 2.52 (s, 3H) 1.89 (br. s., 1H) 1.66 (br. s., 1H) 0.81 (s, 6H)-0.08 (d, J=5.68 Hz, 9H). ES-LCMS: 434.20 m/z (M+H)+.

Intermediate 13

N-(4-hydroxy-2-phenylbutyl)-N-methylbenzenesulfonamide

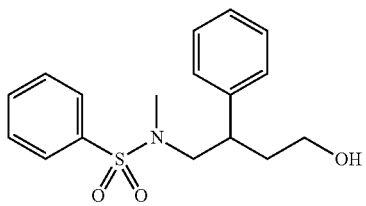 [SMILES: CN(CC(CCO)c1ccccc1)S(=O)(=O)c1ccccc1]

To a solution of N-(4-{[(1,1-dimethylethyl)(dimethyl)silyl]oxy}-2-phenylbutyl)-N-methylbenzenesulfonamide 12 (432 mg, 1.0 mmol) in dry THF (5 mL) was added glacial acetic acid (0.75 mL) followed by tetrabutylammonium fluoride as a 1M solution in THF (1.5 mL) and the solution stirred at room temperature for 18 h. The reaction was poured into saturated NaHCO$_3$ and extracted with ethyl acetate. The organic layer was dried (MgSO$_4$) and concentrated in vacuo to give 13 in quantitative yield.

1H NMR (400 MHz, DMSO-d$_6$) d ppm 7.62-7.74 (m, 3H) 7.52-7.62 (m, 2H) 7.23-7.33 (m, 2H) 7.14-7.24 (m, 3H) 4.38 (t, J=5.13 Hz, 1H) 3.09-3.27 (m, 3H) 2.93-3.08 (m, 2H) 2.52 (s, 3H) 1.84 (br. s., 1H) 1.64 (br. s., 1H). ES-LCMS: 320.11 m/z (M+H)+.

Intermediate 14

N-methyl-N-(4-oxo-2-phenylbutyl)benzenesulfonamide

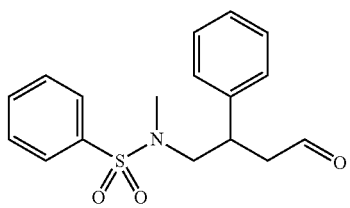 [SMILES: CN(CC(CC=O)c1ccccc1)S(=O)(=O)c1ccccc1]

To a solution of N-(4-hydroxy-2-phenylbutyl)-N-methylbenzenesulfonamide 13 (317 mg, 1.0 mmol) in dry CH$_2$Cl$_2$ (12 mL) was added Dess-Martin Periodinane (840 mg, 2.0 mmol) and the solution stirred at room temperature under nitrogen atmosphere for 1.5 h. The reaction was poured into an aqueous solution of Na$_2$S$_2$O$_3$ (30 mL) and saturated NaHCO$_3$ (15 mL) and stirred for 10 minutes. The solution was extracted with CH$_2$Cl$_2$, the organic layers combined and dried (MgSO$_4$) and concentrated in vacuo. The residue was purified by silica gel chromatography eluting with 10-70% hexanes/ethyl acetate to give 14 (269 mg, 85% yield) as a clear oil.

1H NMR (400 MHz, DMSO-d$_6$) d ppm 9.59 (t, J=1.65 Hz, 1H) 7.63-7.76 (m, 3H) 7.53-7.63 (m, 2H) 7.24-7.36 (m, 4H) 7.15-7.24 (m, 1H) 3.45-3.59 (m, 1H) 3.11-3.20 (m, 1H) 3.01 (dd, J=13.20, 7.52 Hz, 1H) 2.86 (dd, J=5.96, 1.37 Hz, 1H) 2.73 (dd, J=8.34, 2.11 Hz, 1H) 2.56 (s, 3H).

Example 3

3-cyano-N-{4-[(1R,5S)-3-(2-methyl-1H-benzimidazol-1-yl)-8-azabicyclo[3.2.1]oct-8-yl]-2-phenylbutyl}benzenesulfonamide

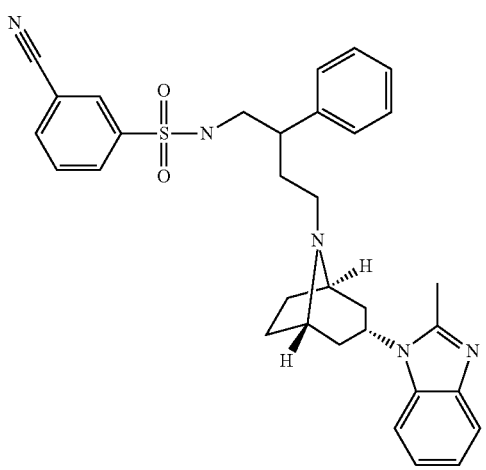 [SMILES: Cc1nc2ccccc2n1[C@H]1C[C@H]2CC[C@@H](C1)N2CCC(CNS(=O)(=O)c1cccc(C#N)c1)c1ccccc1]

To a solution of 3-cyanobenzenesulfonyl chloride (39 mg, 0.19 mmol) in dry CH$_2$Cl$_2$ (1 mL) was added a solution of intermediate 6 (75 mg, 0.19 mmol) in dry CH$_2$Cl$_2$ (2 mL)

followed by diisopropylethylamine (0.085 mL, 0.48 mmol) and the solution stirred at room temperature under nitrogen atmosphere for 1 h. The reaction was concentrated in vacuo and purified by silica gel chromatography eluting with 0-5% CH$_2$Cl$_2$/MeOH to give the title compound (77 mg, 73% yield) as a white solid.

$^1$H NMR (DMSO-d$_6$, 400 MHz) δ 8.08 (d, J=8.98 Hz, 2H), 8.02 (d, J=8.25 Hz, 1H), 7.93 (t, J=5.87 Hz, 1H), 7.76 (t, J=7.88 Hz, 1H), 7.48 (d, J=7.33 Hz, 1H), 7.38 (d, J=7.33 Hz, 1H), 7.23-7.29 (m, 2H), 7.14-7.21 (m, 3H), 7.06-7.13 (m, 2H), 4.53-4.65 (m, 1H), 3.19-3.29 (m, 2H), 2.95-3.09 (m, 2H), 2.78-2.87 (m, 1H), 2.50 (s, 3H), 2.28-2.42 (m, 2H), 1.89-2.01 (m, 4H), 1.74-1.88 (m, 3H), 1.52-1.67 (m, 3H). HRMS: (M+H)$^+$ calcd for C$_{32}$H$_{35}$N$_5$O$_2$S+H, 554.2584. found, 554.2586.

Example 4

4-cyano-N-{4-[(1R,5S)-3-(2-methyl-1H-benzimidazol-1-yl)-8-azabicyclo[3.2.1]oct-8-yl]-2-phenylbutyl}benzenesulfonamide

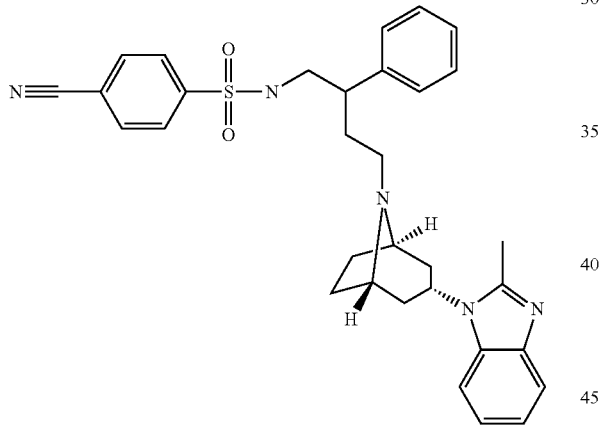

To a solution of 4-cyanobenzenesulfonyl chloride (39 mg, 0.19 mmol) in dry CH$_2$Cl$_2$ (1 mL) was added a solution of intermediate 6 (75 mg, 0.19 mmol) in dry CH$_2$Cl$_2$ (2 mL) followed by diisopropylethylamine (0.085 mL, 0.48 mmol) and the solution stirred at room temperature under nitrogen atmosphere for 1 h. The reaction was concentrated in vacuo and purified by silica gel chromatography eluting with 0-5% CH$_2$Cl$_2$/MeOH to give the title compound (80 mg, 76% yield) as a white solid.

$^1$H NMR (DMSO-d$_6$, 400 MHz) δ 8.00-8.05 (m, overlapping signals, 3H), 7.87 (d, J=8.61 Hz, 2H), 7.48 (d, J=7.33 Hz, 1H), 7.38 (d, J=7.33 Hz, 1H), 7.26 (t, J=7.15 Hz, 2H), 7.14-7.21 (m, 3H), 7.06-7.14 (m, 2H), 4.53-4.65 (m, 1H), 3.19-3.28 (m, 2H), 2.92-3.06 (m, 2H), 2.80-2.88 (m, 1H), 2.50 (s, 3H), 2.28-2.42 (m, 2H), 1.90-2.00 (m, 4H), 1.74-1.88 (m, 3H), 1.52-1.68 (m, 3H). HRMS: (M+H)$^+$ calcd for C$_{32}$H$_{35}$N$_5$O$_2$S+H, 554.2584. found, 554.2588.

Example 5

N-{4-[(1R,5S)-3-(2-methyl-1H-benzimidazol-1-yl)-8-azabicyclo[3.2.1]oct-8-yl]-2-phenylbutyl}methanesulfonamide

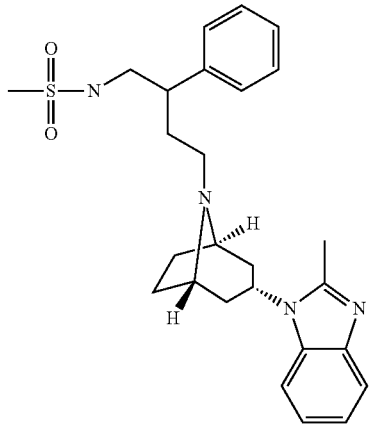 [SMILES: Cc1nc2ccccc2n1[C@H]1C[C@H]2CC[C@@H](C1)N2CCC(CNS(C)(=O)=O)c1ccccc1]

To a solution of intermediate 6 (60 mg, 0.15 mmol) in dry CH$_2$Cl$_2$ (1.5 mL) was added diisopropylethylamine (0.065 mL, 0.38 mmol) and the reaction cooled to 0° C. A solution of methanesulfonyl chloride (0.012 mL, 0.15 mmol) in dry CH$_2$Cl$_2$ (1 mL) was added and the reaction warmed to room temperature and stirred under nitrogen atmosphere for 1 h. The reaction was concentrated in vacuo and purified by silica gel chromatography eluting with 0-5% CH$_2$Cl$_2$/MeOH to give the title compound (46 mg, 66% yield) as a white solid.

$^1$H NMR (DMSO-d$_6$, 400 MHz) δ 7.46 (d, J=7.51 Hz, 1H), 7.36 (d, J=7.87 Hz, 1H), 7.29 (t, J=7.33 Hz, 2H), 7.23 (d, J=7.14 Hz, 2H), 7.18 (t, J=7.14 Hz, 1H), 7.00-7.12 (m, 3H), 4.53-4.65 (m, 1H), 3.05-3.19 (m, 2H), 2.84-2.93 (m, 1H), 2.72 (s, 3H), 2.48 (s, 3H), 2.27-2.42 (m, 2H), 1.98-2.06 (m, 2H), 1.87-1.98 (m, 3H), 1.77 (t, J=11.35 Hz, 2H), 1.56-1.67 (m, 3H). HRMS: (M+H)$^+$ calcd for C$_{26}$H$_{34}$N$_4$O$_2$S+H, 467.2481. found, 467.2487.

Example 6

3-[({4-[(1R,5S)-3-(2-methyl-1H-benzimidazol-1-yl)-8-azabicyclo[3.2.1]oct-8-yl]-2-phenylbutyl}amino)sulfonyl]benzamide

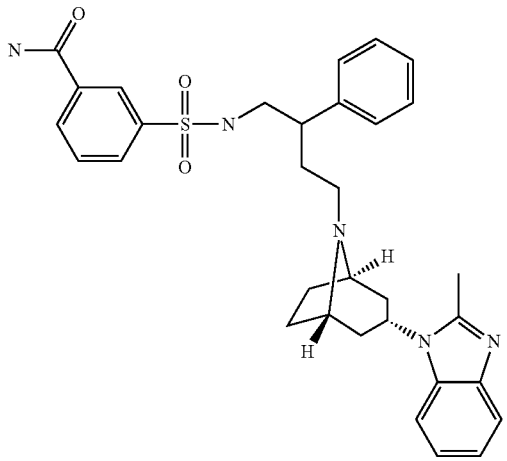 [SMILES: Cc1nc2ccccc2n1[C@H]1C[C@H]2CC[C@@H](C1)N2CCC(CNS(=O)(=O)c1cccc(C(N)=O)c1)c1ccccc1]

The title compound from example 3 (65 mg, 0.12 mmol) was dissolved in acetone (1 mL) and water (0.5 mL). To the solution was added urea hydrogen peroxide (110 mg, 1.2 mmol) followed by $K_2CO_3$ (5 mg, 0.036 mmol) and the reaction stirred at room temperature for 2 h, whereupon the reaction was found to be mostly complete by LC-MS. The reaction was poured into water and extracted with EtOAc. The organic layer was dried ($MgSO_4$) and concentrated in vacuo. The residue was purified by reverse-phase HPLC eluting with 10-90% water/acetonitrile/0.1% TFA. The title compound (37 mg, 54% yield) was obtained as a white solid (free-based with $K_2CO_3$).

1H NMR (400 MHz, DMSO-$d_6$) d ppm 8.24 (s, 1H) 8.16 (br. s., 1H) 8.05 (d, J=7.69 Hz, 1H) 7.85 (d, J=7.87 Hz, 1H) 7.79 (t, J=5.68 Hz, 1H) 7.61 (t, J=7.69 Hz, 1H) 7.55 (br. s., 1H) 7.46 (d, J=7.51 Hz, 1H) 7.35 (d, J=7.69 Hz, 1H) 7.24 (t, J=7.14 Hz, 2H) 7.10-7.20 (m, 3H) 7.08 (t, J=7.97 Hz, 2H) 4.48-4.64 (m, 1H) 3.13-3.25 (m, 2H) 2.85-3.06 (m, 2H) 2.79 (br. s., 2H) 2.47 (s, 3H) 2.24-2.42 (m, 2H) 1.91 (d, J=6.59 Hz, 4H) 1.43-1.68 (m, 2H). HRMS: (M+H)$^+$ calcd for $C_{32}H_{37}N_5O_3S$+H, 572.2695. found, 572.2687.

Example 7

N-{4-{4-[(1R,5S)-3-(2-methyl-1H-benzimidazol-1-yl)-8-azabicyclo[3.2.1]oct-8-yl]-2-phenylbutyl}-2-oxo-2,3-dihydro-1,3-benzoxazole-6-sulfonamide

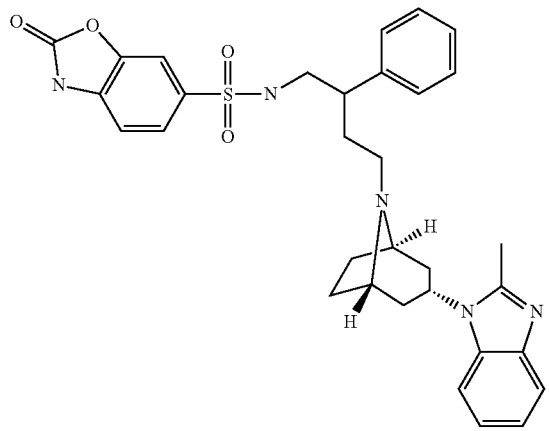 [SMILES: Cc1nc2ccccc2n1[C@H]1C[C@H]2CC[C@@H](C1)N2CCC(CNS(=O)(=O)c1ccc2[nH]c(=O)oc2c1)c1ccccc1]

To a solution of 2-oxo-2,3-dihydro-1,3-benzoxazole-6-sulfonyl chloride (35 mg, 0.15 mmol) in dry $CH_2Cl_2$ (1 mL) was added a solution of intermediate 6 (60 mg, 0.15 mmol) in dry $CH_2Cl_2$ (2 mL) followed by diisopropylethylamine (0.065 mL, 0.38 mmol) and the solution stirred at room temperature under nitrogen atmosphere for 1 h. The reaction was concentrated in vacuo and purified by silica gel chromatography eluting with 0-5% $CH_2Cl_2$/MeOH, followed by reverse-phase HPLC eluting with 10-90% water/acetonitrile/ 0.1% TFA to give the title compound (56 mg, 53% yield) as the TFA salt.

1H NMR (400 MHz, DMSO-$d_6$) d ppm 12.11 (s, 1H) 9.21 (br. s., 1H) 7.74 (d, J=5.49 Hz, 2H) 7.66 (s, 1H) 7.49-7.59 (m, 2H) 7.46 (br. s., 2H) 7.28 (t, J=7.23 Hz, 2H) 7.18 (t, J=8.88 Hz, 3H) 5.04 (br. s., 1H) 3.95-4.16 (m, 2H) 2.80-3.05 (m, 2H) 2.69 (s, 3H) 2.17 (br. s., 3H). HRMS: (M+H)$^+$ calcd for $C_{32}H_{35}N_5O_4S$+H, 586.2488. found, 586.2480.

Example 8

4-[({4-[(1R,5S)-3-(2-methyl-1H-benzimidazol-1-yl)-8-azabicyclo[3.2.1]oct-8-yl]-2-phenylbutyl}amino)sulfonyl]benzamide

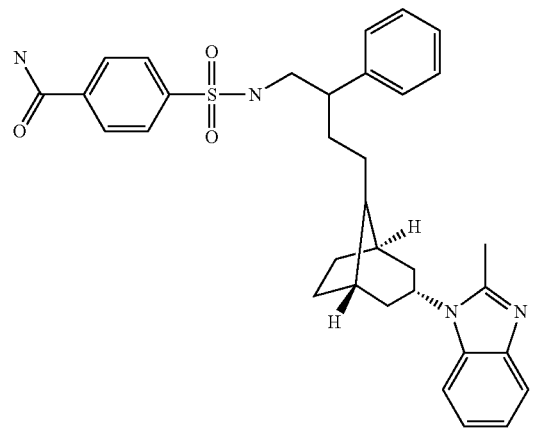 [SMILES: Cc1nc2ccccc2n1[C@H]1C[C@H]2CC[C@@H](C1)C2CCC(CNS(=O)(=O)c1ccc(C(N)=O)cc1)c1ccccc1]

To a suspension of the title compound from example 4 (63 mg, 0.11 mmol) in t-butanol (1 mL) was added 1M NaOH (0.28 mL) and the reaction stirred at room temperature for 2 h, followed by heating to 80° C. for 2 h. The reaction was cooled to room temperature and partitioned between ethyl acetate and pH 8 buffer solution. The organic layer was dried ($MgSO_4$) and concentrated in vacuo. The residue was purified by reverse-phase HPLC eluting with 10-90% water/acetonitrile/0.1% TFA. The title compound (40 mg, 63% yield) was obtained as a white solid (free-based with $K_2CO_3$).

$^1$H NMR (DMSO-$d_6$, 400 MHz) δ 8.13 (s, 1H), 8.00 (d, J=8.43 Hz, 2H), 7.79-7.87 (m, 3H), 7.58 (s, 1H), 7.48 (d, J=7.33 Hz, 1H), 7.38 (d, J=8.07 Hz, 1H), 7.24-7.31 (m, 2H), 7.15-7.23 (m, 3H), 7.06-7.14 (m, 2H), 4.53-4.65 (m, 1H), 3.18-3.26 (m, 2H), 2.90-3.02 (m, 2H), 2.80-2.89 (m, 1H), 2.50 (s, 3H), 2.29-2.43 (m, 3H), 1.90-1.99 (m, 3H), 1.73-1.87 (m, 3H), 1.50-1.68 (m, 3H). HRMS: (M+H)$^+$ calcd for $C_{32}H_{37}N_5O_3S$+H, 572.2690. found, 572.2690.

Example 9 dimethyl{4-[(1R,5S)-3-(2-methyl-1H-benzimidazol-1-yl)-8-azabicyclo[3.2.1]oct-8-yl]-2-phenylbutyl}amidophosphate

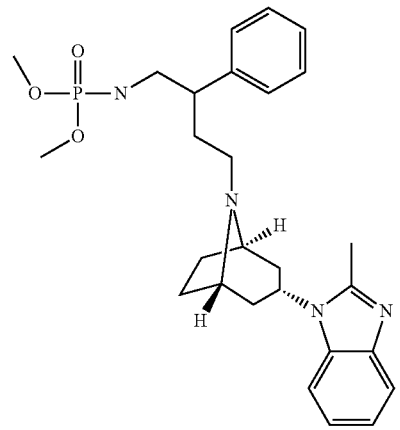 [SMILES: COP(=O)(NCC(CCN1[C@@H]2CC[C@H]1C[C@@H](n1c(C)nc3ccccc31)C2)c1ccccc1)OC]

To a solution of intermediate 6 (65 mg, 0.17 mmol) in dry CH$_2$Cl$_2$ (1.5 mL) was added diisopropylethylamine (0.075 mL, 0.42 mmol) and the reaction cooled to 0° C. A solution of dimethyl chloridophosphate (0.018 mL, 0.17 mmol) was added and the reaction warmed to room temperature and stirred under nitrogen atmosphere for 1 h. The reaction was concentrated in vacuo and purified by silica gel chromatography eluting with 0-6% CH$_2$Cl$_2$/MeOH to give the title compound (36 mg, 43% yield) as a white solid.

$^1$H NMR (DMSO-d$_6$, 400 MHz) δ 7.46 (d, J=7.51 Hz, 1H), 7.36 (d, J=7.51 Hz, 1H), 7.28 (t, J=7.32 Hz, 2H), 7.13-7.23 (m, 3H), 7.04-7.13 (m, 2H), 4.87-4.96 (m, 1H), 4.52-4.65 (m, 1H), 3.36 (dd, J=24.87, 11.17 Hz, 6H), 2.82-3.02 (m, 3H), 2.73-2.82 (m, 1H), 2.48 (s, 3H), 2.26-2.42 (m, 2H), 1.86-2.04 (m, 5H), 1.72-1.82 (m, 3H), 1.54-1.67 (m, 3H). HRMS: (M+H)$^+$ calcd for C$_{27}$H$_{37}$N$_4$O$_3$P+H, 497.2676. found, 497.2676.

Example 10

2,2,2-trifluoro-N-{4-[(1R,5S)-3-(2-methyl-1H-benz-imidazol-1-yl)-8-azabicyclo[3.2.1]oct-8-yl]-2-phenylbutyl}ethanesulfonamide

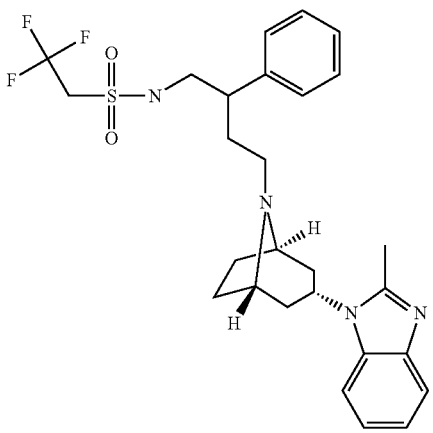 [SMILES: Cc1nc2ccccc2n1[C@H]1C[C@H]2CC[C@@H](C1)N2CCC(CNS(=O)(=O)CC(F)(F)F)c1ccccc1]

To a solution of intermediate 6 (65 mg, 0.17 mmol) in dry CH$_2$Cl$_2$ (1.5 mL) was added diisopropylethylamine (0.075 mL, 0.42 mmol) and the reaction cooled to 0° C. A solution of 2,2,2-trifluoroethanesulfonyl chloride (0.019 mL, 0.17 mmol) was added and the reaction warmed to room temperature and stirred under nitrogen atmosphere for 1 h. The reaction was concentrated in vacuo and purified by silica gel chromatography eluting with 0-6% CH$_2$Cl$_2$/MeOH to give the title compound (33 mg, 37% yield) as a white solid.

$^1$H NMR (DMSO-d$_6$, 400 MHz) δ 7.83 (t, J=5.49 Hz, 1H), 7.46 (d, J=7.51 Hz, 1H), 7.36 (d, J=7.51 Hz, 1H), 7.26-7.33 (m, 2H), 7.16-7.26 (m, 3H), 7.03-7.13 (m, 2H), 4.54-4.66 (m, 1H), 4.14-4.25 (m, 2H), 3.06-3.21 (m, 3H), 2.92 (br s, 1H), 2.48 (s, 3H), 2.27-2.42 (m, 2H), 1.87-2.05 (m, 5H), 1.77 (t, J=11.35 Hz, 2H), 1.55-1.69 (m, 2H), 1.21 (t, J=6.04 Hz, 2H). HRMS: (M+H)$^+$ calcd for C$_{27}$H$_{33}$F$_3$N$_4$O$_2$S+H, 535.2349. found, 535.2348.

Example 11

N-{4-[(1R,5S)-3-(2-methyl-3H-imidazo[4,5-c]pyridin-3-yl)-8-azabicyclo[3.2.1]oct-8-yl]-2-phenylbutyl}benzenesulfonamide

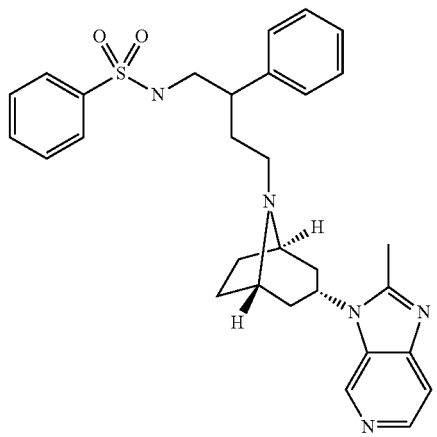 [SMILES: Cc1nc2ccncc2n1[C@H]1C[C@H]2CC[C@@H](C1)N2CCC(CNS(=O)(=O)c1ccccc1)c1ccccc1]

To a solution of intermediate 17 (102 mg, 0.25 mmol) in CH$_2$Cl$_2$ (2.5 mL) was added 3-[(3-endo)-8-azabicyclo[3.2.1]oct-3-yl]-2-methyl-3H-imidazo[4,5-c]pyridine (61 mg, 0.25 mmol) prepared as previously described in WO 2005/101989 A2, followed by NaBH(OAc)$_3$ (106 mg, 0.5 mmol) and the solution stirred at room temperature for 18 h under an atmosphere of nitrogen. The reaction was poured into aqueous K$_2$CO$_3$ and extracted with CH$_2$Cl$_2$ and the organic layer dried (MgSO$_4$) and concentrated in vacuo. The residue was purified by silica gel chromatography eluting with 0-5% CH$_2$Cl$_2$/methanol. The residue was dissolved in CH$_2$Cl$_2$ (1.5 mL), and trifluoroacetic acid (0.3 mL) was added and the reaction stirred at room temperature for 3.5 h. The reaction was poured into aqueous K$_2$CO$_3$ and extracted with CH$_2$Cl$_2$, the organic layer was dried (MgSO$_4$) and concentrated in vacuo to give the title compound (108 mg, 82%) as a white solid.

$^1$H NMR (DMSO-d$_6$, 400 MHz) δ 8.79 (s, 1H), 8.26 (d, J=4.82 Hz, 1H), 7.71-7.79 (m, 4H), 7.51-7.66 (m, 5H), 7.25-7.35 (m, 3H), 7.15-7.25 (m, 3H), 4.65 (br s, 1H), 2.80-3.02 (m, 4H), 2.59 (s, 3H), 1.84-2.03 (m, 5H), 1.52-1.84 (m, 5H). HRMS: (M+H)$^+$ calcd for C$_{30}$H$_{35}$N$_5$O$_2$S+H, 530.2584. found, 530.2584.

Preparation of Intermediate 17

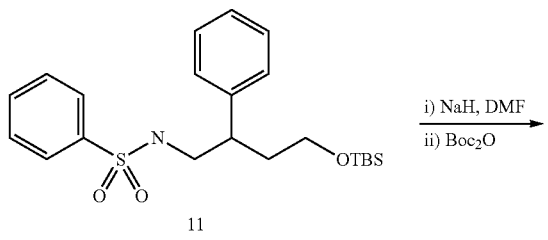

11

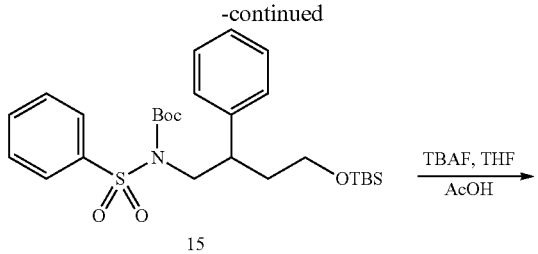

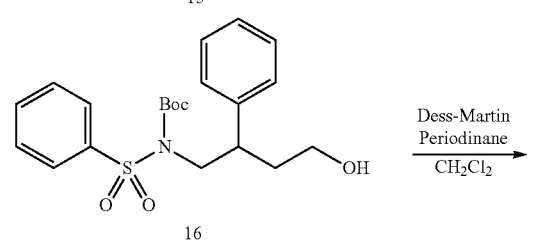

Intermediate 15

1,1-dimethylethyl(4-{[(1,1-dimethylethyl)(dimethyl)silyl]oxy}-2-phenylbutyl)(phenylsulfonyl)carbamate

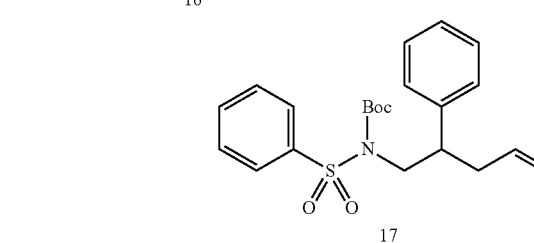

A solution of N-(4-{[(1,1-dimethylethyl)(dimethyl)silyl]oxy}-2-phenylbutyl)benzenesulfonamide 11 (2.67 g, 6.3 mmol) in dry DMF (60 mL) was cooled to 0° C. and a 60% suspension of sodium hydride in mineral oil (280 mg, 7.0 mmol) was added and the reaction stirred at 0° C. for 10 minutes and room temperature for 30 minutes under an atmosphere of nitrogen. Di-tert-butyldicarbonate (1.73 g, 8.0 mmol) was added and the reaction stirred at room temperature for 1 h. Water (5 mL) was added and the reaction poured into ethyl acetate. The organic layer was washed with water and dried (MgSO$_4$) and concentrated in vacuo. The residue was purified by silica gel chromatography eluting with 5-40% hexanes/ethyl acetate to yield 15 (1.82 g, 55%) as an oil.

1H NMR (400 MHz, DMSO-d$_6$) d ppm 7.64-7.78 (m, 3H) 7.56 (t, J=7.72 Hz, 2H) 7.32 (t, J=7.32 Hz, 2H) 7.12-7.28 (m, 3H) 3.97 (d, J=7.62 Hz, 2H) 3.50 (br. s., 1H) 3.28 (br. s., 2H) 1.98 (br. s., 1H) 1.79 (br. s., 1H) 1.16 (s, 9H) 0.83 (s, 9H)-0.07 (d, J=14.05 Hz, 6H). ES-LCMS: m/z 542.15 (M+Na)$^+$.

Intermediate 16

1,1-dimethylethyl(4-hydroxy-2-phenylbutyl)(phenylsulfonyl)carbamate

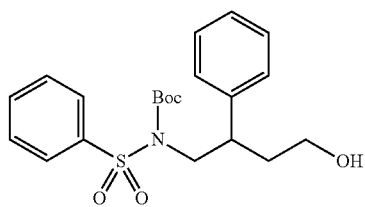 [SMILES: CC(C)(C)OC(=O)N(CC(CCO)c1ccccc1)S(=O)(=O)c1ccccc1]

To a solution of 1,1-dimethylethyl(4-{[(1,1-dimethylethyl)(dimethyl)silyl]oxy}-2-phenylbutyl)(phenylsulfonyl)carbamate 15 (1.82 g, 3.5 mmol) in dry THF (20 mL) was added glacial acetic acid (2.6 mL) followed by tetrabutylammonium fluoride as a 1M solution in THF (5.2 mL) and the solution stirred at room temperature for 18 h. The reaction was poured into saturated NaHCO$_3$ and extracted with ethyl acetate. The organic layer was dried (MgSO$_4$) and concentrated in vacuo to give 16 in quantitative yield.

1H NMR (400 MHz, DMSO-d$_6$) d ppm 7.63-7.77 (m, 3H) 7.55 (t, J=7.62 Hz, 2H) 7.30 (t, 2H) 7.15-7.27 (m, 3H) 4.45 (t, J=4.92 Hz, 1H) 3.97 (d, J=7.62 Hz, 2H) 3.24-3.30 (m, 1H) 3.18 (br. s., 2H) 1.81-1.94 (m, 1H) 1.68-1.81 (m, 1H) 1.16 (d, J=2.41 Hz, 9H). ES-LCMS: 451.23 m/z (M+HCO$_2$)$^-$.

Intermediate 17

1,1-dimethylethyl(4-oxo-2-phenylbutyl)(phenylsulfonyl)carbamate

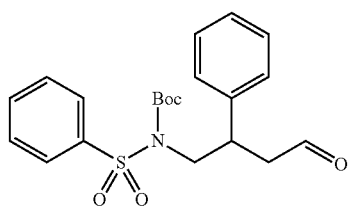 [SMILES: CC(C)(C)OC(=O)N(CC(CC=O)c1ccccc1)S(=O)(=O)c1ccccc1]

To a solution of 1,1-dimethylethyl(4-hydroxy-2-phenylbutyl)(phenylsulfonyl)carbamate 16 (1.42 g, 3.5 mmol) in dry CH$_2$Cl$_2$ (40 mL) was added Dess-Martin Periodinane (3.0 g, 7.0 mmol) and the reaction stirred at room temperature under an atmosphere of nitrogen for 2 h. The reaction was poured into a solution of 5% aqueous Na$_2$S$_2$O$_3$ (90 mL) and saturated NaHCO$_3$ (45 mL) and stirred for 10 min. The aqueous layer was extracted with CH$_2$Cl$_2$ and the organic layer dried (MgSO$_4$) and concentrated in vacuo. The residue was purified by silica gel chromatography eluting with 10-60% hexanes/ethyl acetate to afford 17 (1.16 g, 82%) as a colorless oil.

1H NMR (400 MHz, DMSO-d$_6$) d ppm 9.59 (s, 1H) 7.65-7.81 (m, 3H) 7.57 (t, J=7.72 Hz, 2H) 7.17-7.42 (m, 5H) 4.00 (dd, J=7.42, 5.02 Hz, 2H) 3.57-3.78 (m, 1H) 2.82-2.97 (m, 2H) 1.15 (s, 9H). ES-LCMS: 348.08 m/z (M−tBu)$^+$.

Example 12

N-{4-[(1R,5S)-3-(2-methyl-1H-benzimidazol-1-yl)-8-azabicyclo[3.2.1]oct-8-yl]-2-phenylbutyl}-4-morpholinesulfonamide

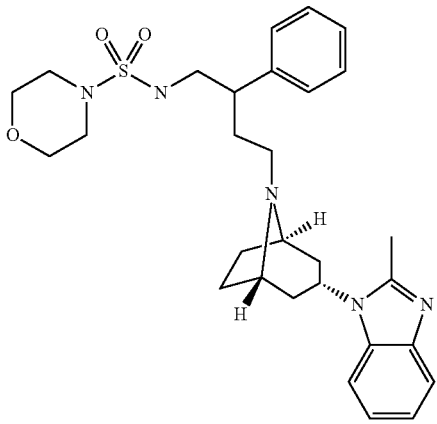 [SMILES: Cc1nc2ccccc2n1[C@H]1C[C@H]2CC[C@@H](C1)N2CCC(CNS(=O)(=O)N1CCOCC1)c1ccccc1]

To a solution of intermediate 6 (61 mg, 0.16 mmol) in dry CH$_2$Cl$_2$ (2 mL) was added diisopropylethylamine (0.070 mL, 0.4 mmol). A solution of 4-morpholinesulfonyl chloride (0.022 mL, 0.16 mmol) was added and the reaction stirred at room temperature under nitrogen atmosphere for 1.5 h and then heated to 35° C. for 18 h. The reaction was concentrated in vacuo and purified by reverse-phase HPLC eluting with 10-90% water/acetonitrile/0.1% TFA. to give the title compound (55 mg, 64% yield) as a white solid (free-based with K$_2$CO$_3$).

1H NMR (400 MHz, DMSO-d$_6$) d ppm 7.50 (d, J=7.42 Hz, 1H) 7.39 (br. s., 3H) 7.32 (d, J=7.42 Hz, 3H) 7.18-7.29 (m, 4H) 7.05-7.18 (m, 3H) 4.64 (br. s., 1H) 3.01-3.23 (m, 3H) 2.78-3.01 (m, 5H) 2.53 (s, 3H) 2.29-2.46 (m, 3H) 1.90-2.11 (m, 3H) 1.74-1.88 (m, 3H) 1.59-1.73 (m, 4H)). HRMS: (M+H)$^+$ calcd for C$_{29}$H$_{39}$N$_5$O$_3$S+H, 538.2852. found, 538.2849

Example 13

N-{4-[(1R,5S)-3-(5-acetyl-2-methyl-4,5,6,7-tetrahydro-3H-imidazo[4,5-c]pyridin-3-yl)-8-azabicyclo[3.2.1]oct-8-yl]-2-phenylbutyl}benzenesulfonamide

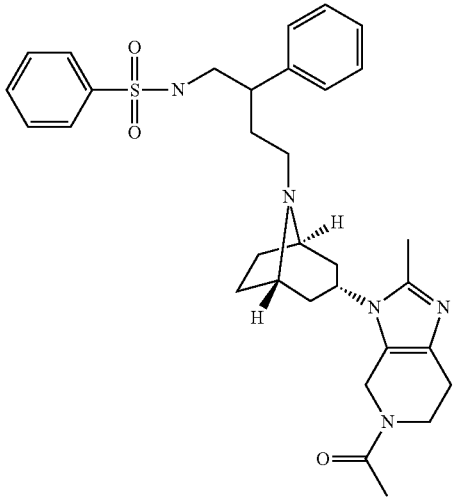 [SMILES: CC(=O)N1CCc2nc(C)n([C@H]3C[C@H]4CC[C@@H](C3)N4CCC(CNS(=O)(=O)c3ccccc3)c3ccccc3)c2C1]

To a solution of intermediate 17 (75 mg, 0.19 mmol) in CH$_2$Cl$_2$ (2 mL) was added 5-acetyl-3-[(3-endo)-8-azabicyclo[3.2.1]oct-3-yl]-2-methyl-4,5,6,7-tetrahydro-3H-imidazo[4,5-c]pyridine (59 mg, 0.2 mmol) prepared as previously described in WO 2005/101989 A2, followed by NaBH(OAc)$_3$ (80 mg, 0.37 mmol) and the solution stirred at room temperature for 18 h under an atmosphere of nitrogen. The reaction was poured into aqueous K$_2$CO$_3$ and extracted with CH$_2$Cl$_2$ and the organic layer dried (MgSO$_4$) and concentrated in vacuo. The residue was purified by silica gel chromatography eluting with 0-6% CH$_2$Cl$_2$/methanol. The residue was dissolved in CH$_2$Cl$_2$ (1.5 mL), and trifluroacetic acid (0.3 mL) was added and the reaction stirred at room temperature for 2.5 h. The reaction was poured into aqueous K$_2$CO$_3$ and extracted with CH$_2$Cl$_2$, the organic layer was dried (MgSO$_4$) and concentrated in vacuo to give the title compound (49 mg, 46%) as a white solid.

1H NMR (400 MHz, DMSO-d$_6$) d ppm 7.75 (d, J=7.22 Hz, 2H) 7.69-7.75 (m, 1H) 7.52-7.66 (m, 3H) 7.23-7.34 (m, 2H) 7.11-7.24 (m, 3H) 4.51 (s, 2H) 4.27 (br. s., 1H) 3.56-3.70 (m, 2H) 3.11-3.27 (m, 1H) 2.74-3.00 (m, 3H) 2.32 (br. s., 2H) 2.22-2.29 (m, 3H) 2.02-2.14 (m, 3H) 1.91 (br. s., 5H) 1.28-1.64 (m, 6H). HRMS: (M+H)$^+$ calcd for C$_{32}$H$_{41}$N$_5$O$_3$S+H, 576.3008. found, 576.3002.

Example 14

N-cyclobutyl-N'-{4-[(1R,5S)-3-(2-methyl-1H-benzimidazol-1-yl)-8-azabicyclo[3.2.1]oct-8-yl]-2-phenylbutyl}sulfamide

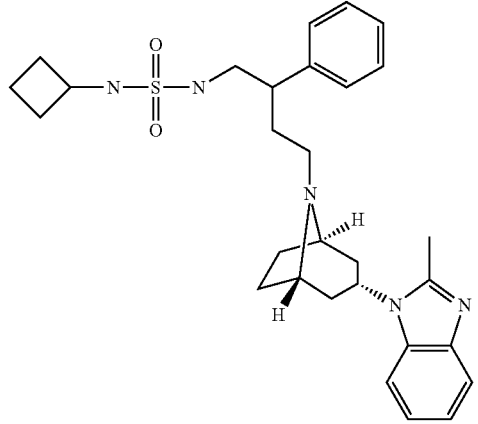 [SMILES: Cc1nc2ccccc2n1[C@H]1C[C@H]2CC[C@@H](C1)N2CCC(CNS(=O)(=O)NC1CCC1)c1ccccc1]

To a solution of intermediate 6 (73 mg, 0.19 mmol) in acetonitrile (1.5 mL) was added N-cyclobutyl-2-oxo-1,3-oxazolidine-3-sulfonamide (46 mg, 0.2 mmol), prepared as described in Org. Proc. R & D, 2006, pp. 770-775, followed by diisopropylethylamine (0.085 mL, 0.47 mmol) and the solution heated to 80° C. for 5 h. The reaction was concentrated in vacuo and the residue purified by reverse-phase HPLC eluting with 10-90% water/acetonitrile/0.1% TFA. to give the title compound (70 mg, 70% yield) as a white solid (free-based with K$_2$CO$_3$).

1H NMR (400 MHz, DMSO-d$_6$) d ppm 7.45 (d, J=1.10 Hz, 1H) 7.36 (d, J=7.51 Hz, 1H) 7.24-7.32 (m, 2H) 7.16-7.24 (m, 3H) 6.97-7.16 (m, 4H) 6.79 (t, J=5.40 Hz, 1H) 4.49-4.68 (m, 1H) 3.38-3.54 (m, 1H) 2.78-3.03 (m, 3H) 2.48 (s, 3H) 2.25-2.42 (m, 2H) 1.86-2.17 (m, 5H) 1.69-1.87 (m, 5H) 1.53-1.69 (m, 4H) 1.35-1.55 (m, 3H). HRMS: (M+H)$^+$ calcd for C$_{29}$H$_{39}$N$_5$O$_2$S+H, 522.2903. found, 522.2903.

Example 15

N-(4,4-difluorocyclohexyl)-N'-{4-[(1R,5S)-3-(2-methyl-1H-benzimidazol-1-yl)-8-azabicyclo[3.2.1]oct-8-yl]-2-phenylbutyl}sulfamide

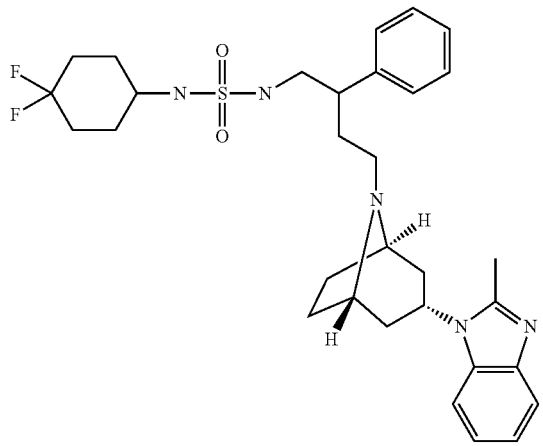 [SMILES: Cc1nc2ccccc2n1[C@H]1C[C@H]2CC[C@@H](C1)N2CCC(CNS(=O)(=O)NC1CCC(F)(F)CC1)c1ccccc1]

To a solution of intermediate 6 (65 mg, 0.17 mmol) in acetonitrile (1.5 mL) was added N-(4,4-difluorocyclohexyl)-2-oxo-1,3-oxazolidine-3-sulfonamide (43 mg, 0.15 mmol), prepared as described in *Org. Proc. R & D,* 2006, pp. 770-775, followed by diisopropylethylamine (0.065 mL, 0.38 mmol) and the solution heated to 80° C. for 4 h. The reaction was concentrated in vacuo and the residue purified by silica gel chromatography eluting with 0-5% dichloromethane/methanol to give the title compound (63 mg, 72% yield) as a white solid.

1H NMR (400 MHz, DMSO-$d_6$) d ppm 7.50 (d, J=7.42 Hz, 1H) 7.40 (d, J=7.83 Hz, 1H) 7.29-7.37 (m, 3H) 7.18-7.28 (m, 3H) 7.06-7.18 (m, 2H) 6.87-6.99 (m, 2H) 4.53-4.71 (m, 1H) 3.33 (br. s., 2H) 2.88-3.12 (m, 3H) 2.53 (s, 3H) 2.30-2.46 (m, 2H) 1.88-2.11 (m, 7H) 1.58-1.88 (m, 8H) 1.46 (br. s., 2H).). HRMS: (M+H)$^+$ calcd for $C_{31}H_{41}N_5O_2F_2S$+H, 586.3027. found, 586.3021.

Example 16

4,4-difluoro-N-(4-{(1R,5S)-3-[3-methyl-5-(1-methylethyl)-4H-1,2,4-triazol-4-yl]-8-azabicyclo[3.2.1]oct-8-yl}-2-phenylbutyl)cyclohexanecarboxamide

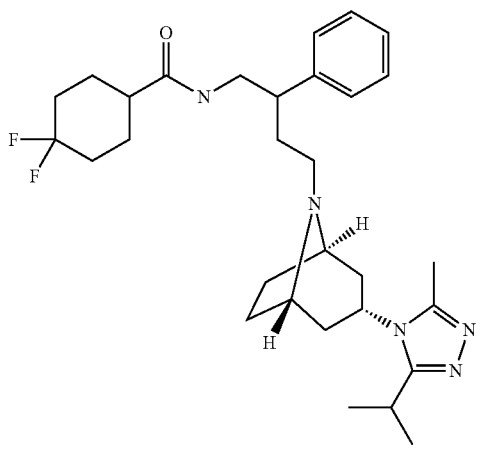 [SMILES: Cc1nnc(C(C)C)n1[C@H]1C[C@H]2CC[C@@H](C1)N2CCC(CNC(=O)C1CCC(F)(F)CC1)c1ccccc1]

To a solution of 4,4-difluorocyclohexanecarboxylic acid (26 mg, 0.16 mmol) in CH$_2$Cl$_2$ (1 mL) was added HATU (60 mg, 0.16 mmol) followed by diisopropylethylamine (0.045 mL, 0.26 mmol) and the solution stirred at room temperature for 10 minutes under an atmosphere of nitrogen. A solution of intermediate 19 (50 mg, 0.13 mmol) in CH$_2$Cl$_2$ (1.3 mL) was added to the reaction and stirred at room temperature for 18 h. The reaction was concentrated in vacuo and purified by reverse-phase chromatography eluting with 10-100% water/acetonitrile/0.1% TFA to give the title compound (80 mg, 96%) isolated as the trifluoroacetate salt.

1H NMR (400 MHz, DMSO-$d_6$) d ppm 9.47 (br s, 1H), 7.80 (t, J=5.96 Hz, 1H) 7.28-7.38 (m, 2H) 7.17-7.28 (m, 3H) 4.74-4.92 (m, 1H) 4.08 (br. s., 2H) 3.92-4.04 (m, 2H) 3.27-3.44 (m, 2H) 3.15-3.28 (m, 2H) 3.04-3.14 (m, 2H) 2.97 (br. s., 2H) 2.82 (br. s., 2H) 2.60-2.77 (m, 4H) 2.58 (s, 3H) 2.08-2.35 (m, 2H) 1.84-2.08 (m, 4H) 1.39-1.82 (m, 3H) 1.26 (dd, J=6.78, 2.93 Hz, 6H). HRMS: (M+H)$^+$ calcd for $C_{30}H_{43}F_2N_5O$+H, 528.3508. found, 528.3507.

Preparation of Intermediate 19

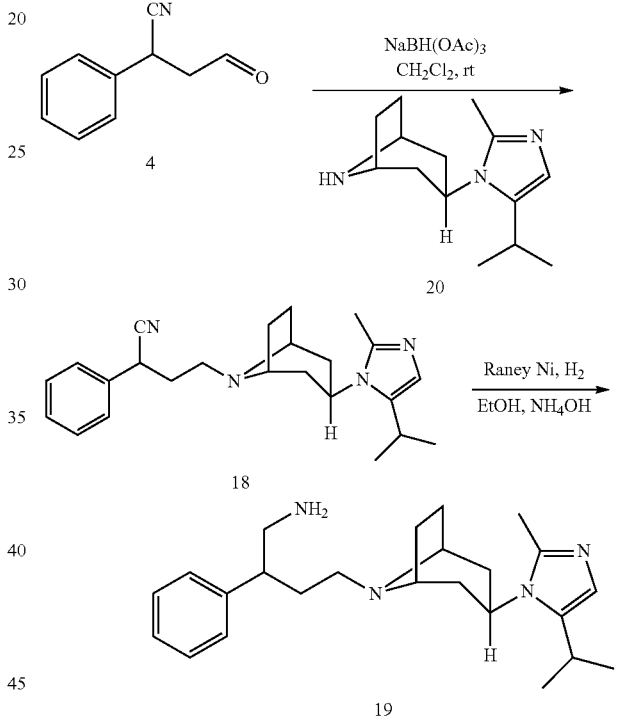

Intermediate 18

4-{3-[2-methyl-5-(1-methylethyl)-1H-imidazol-1-yl]-8-azabicyclo[3.2.1]oct-8-yl}-2-phenylbutanenitrile

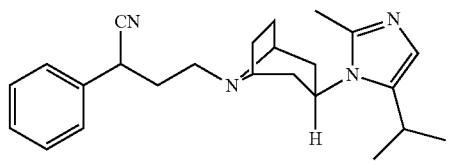 [SMILES: Cc1ncc(C(C)C)n1C1CC2CCC(C1)N2CCC(C#N)c1ccccc1]

To a solution of intermediate 4 (500 mg, 3.1 mmol) in CH$_2$Cl$_2$ (30 mL) was added 3-[2-methyl-5-(1-methylethyl)-1H-imidazol-1-yl]-8-azabicyclo[3.2.1]octane 20 (810 mg, 3.4 mmol) prepared as previously described in WO 2005/

101989, followed by NaBH(OAc)$_3$ (1.30 g, 6.2 mmol) and the solution stirred at room temperature for 18 h under an atmosphere of nitrogen. The reaction was poured into aqueous K$_2$CO$_3$ and extracted with CH$_2$Cl$_2$ and the organic layer dried (MgSO$_4$) and concentrated in vacuo. The residue was purified by silica gel chromatography eluting with 0-6% CH$_2$Cl$_2$/methanol to give 18 (1.09 g, 93%) as a white solid.

1H NMR (400 MHz, DMSO-d$_6$) d ppm 7.39-7.46 (m, 5H) 7.30-7.37 (m, J=8.68, 4.41, 4.41, 4.12 Hz, 1H) 4.42-4.58 (m, 1H) 4.34 (dd, J=8.43, 5.68 Hz, 1H) 3.07 (quin, J=6.78 Hz, 1H) 2.39-2.46 (m, 2H) 2.36 (s, 3H) 2.22 (t, J=6.32 Hz, 2H) 1.86-2.11 (m, 5H) 1.45-1.68 (m, 5H) 1.23 (dd, J=6.78, 4.22 Hz, 6H). ES-LCMS: 378.22 m/z (M+H)$^+$.

Intermediate 19

4-{3-[2-methyl-5-(1-methylethyl)-1H-imidazol-1-yl]-8-azabicyclo[3.2.1]oct-8-yl}-2-phenyl-1-butanamine

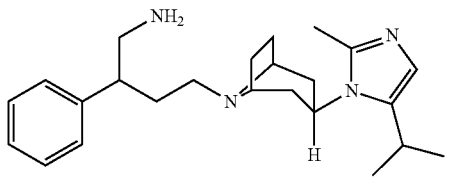 [SMILES: Cc1ncc(C(C)C)n1C1CC2CCC(C1)N2CCC(CN)c1ccccc1]

To a solution of 4-{3-[2-methyl-5-(1-methylethyl)-1H-imidazol-1-yl]-8-azabicyclo[3.2.1]oct-8-yl}-2-phenylbutanenitrile 18 (880 mg, 2.3 mmol) in absolute ethanol (30 mL) was added a spatula of Raney Nickel followed by concentrated ammonia (5 mL) and the reaction hydrogenated at 60 psi for 18 h. The catalyst was filtered through celite and the filtrate concentrated in vacuo to give 19 (843 mg, 95%) as a white solid.

1H NMR (400 MHz, DMSO-d$_6$) d ppm 7.22-7.35 (m, 2H) 7.07-7.21 (m, 4H) 4.05-4.23 (m, 1H) 2.93-3.10 (m, 2H) 2.70-2.84 (m, 2H) 2.57-2.70 (m, 2H) 2.27 (s, 3H) 2.15 (t, 2H) 1.69-2.03 (m, 6H) 1.43-1.69 (m, 6H) 1.18 (d, J=6.78 Hz, 6H). ES-LCMS: 382.23 m/z (M+H)$^+$.

Example 17

N-(4-{(1R,5S)-3-[3-methyl-5-(1-methylethyl)-4H-1,2,4-triazol-4-yl]-8-azabicyclo[3.2.1]oct-8-yl}-2-phenylbutyl)benzenesulfonamide

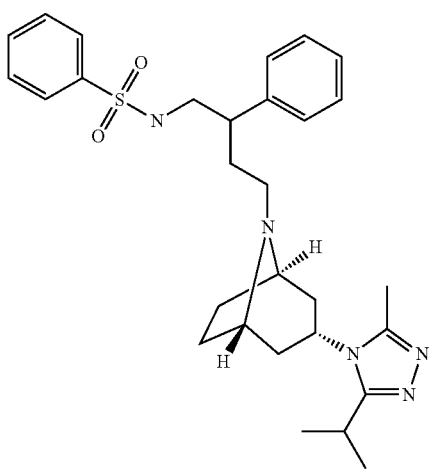 [SMILES: Cc1nnc(C(C)C)n1[C@H]1C[C@H]2CC[C@@H](C1)N2CCC(CNS(=O)(=O)c1ccccc1)c1ccccc1]

To a solution of intermediate 19 (100 mg, 0.26 mmol) in CH$_2$Cl$_2$ (2.6 mL) was added diisopropylethylamine (0.11 mL, 0.65 mmol) followed by phenylsulfonyl chloride (0.033 mL, 0.26 mmol) and the solution stirred at room temperature under nitrogen atmosphere for 18 h. The reaction was concentrated in vacuo and purified by reverse phase chromatography eluting with 10-100% water/acetonitrile/0.1% TFA to give the title compound (103 mg, 76% yield) as a white solid (free-based with K$_2$CO$_3$).

1H NMR (400 MHz, DMSO-d$_6$) d ppm 7.74 (d, J=6.78 Hz, 2H) 7.66-7.72 (m, 1H) 7.50-7.66 (m, 3H) 7.27 (t, J=7.33 Hz, 2H) 7.11-7.23 (m, 3H) 4.26-4.44 (m, 1H) 3.26 (br. s., 2H) 3.20 (br. s., 2H) 2.75-3.06 (m, 7H) 2.34 (s, 3H) 2.20-2.33 (m, 1H) 1.77-1.96 (m, 4H) 1.42-1.57 (m, 2H) 1.23 (dd, J=6.78, 1.65 Hz, 6H). HRMS: (M+H)$^+$ calcd for C$_{29}$H$_{39}$N$_5$O$_2$S+H, 522.2897. found, 522.2901.

Example 18

3,3-difluoro-N-(4-{(1R,5S)-3-[3-methyl-5-(1-methylethyl)-4H-1,2,4-triazol-4-yl]-8-azabicyclo[3.2.1]oct-8-yl}-2-phenylbutyl)cyclobutanecarboxamide

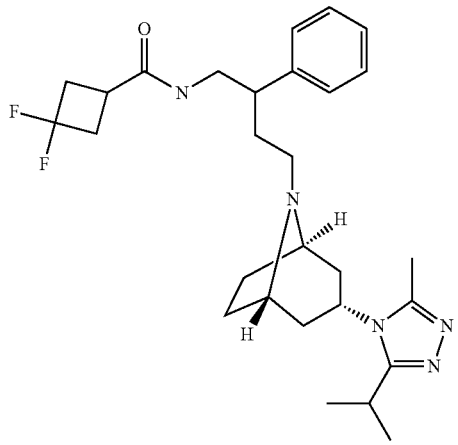 [SMILES: Cc1nnc(C(C)C)n1[C@H]1C[C@H]2CC[C@@H](C1)N2CCC(CNC(=O)C1CC(F)(F)C1)c1ccccc1]

To a solution of 3,3-difluorocyclobutanecarboxylic acid (22 mg, 0.16 mmol) in CH$_2$Cl$_2$ (1 mL) was added HATU (60 mg, 0.16 mmol) followed by diisopropylethylamine (0.045 mL, 0.26 mmol) and the solution stirred at room temperature for 10 minutes under an atmosphere of nitrogen. A solution of intermediate 19 (50 mg, 0.13 mmol) in CH$_2$Cl$_2$ (1.3 mL) was added to the reaction and stirred at room temperature for 18 h. The reaction was concentrated in vacuo and purified by reverse-phase chromatography eluting with 10-100% water/acetonitrile/0.1% TFA to give the title compound (80 mg, 96%) isolated as the trifluoroacetate salt.

1H NMR (400 MHz, DMSO-d$_6$) d ppm 9.33 (br. s., 1H) 7.88-8.05 (m, 1H) 7.26-7.36 (m, 2H) 7.13-7.25 (m, 3H) 4.67-4.91 (m, 1H) 3.28-3.39 (m, 2H) 3.15-3.28 (m, 2H) 2.99-3.13 (m, 2H) 2.94 (br. s., 1H) 2.56-2.84 (m, 6H) 2.54 (s, 3H) 2.09-2.34 (m, 2H) 1.83-2.09 (m, 7H) 1.24 (dd, J=6.59, 2.56 Hz, 6H). HRMS: (M+H)$^+$ calcd for C$_{28}$H$_{39}$F$_2$N$_5$O+H, 500.3195. found, 500.3196.

Example 19

N-{2-methyl-4-[(1R,5S)-3-(2-methyl-1H-benzimidazol-1-yl)-8-azabicyclo[3.2.1]oct-8-yl]-2-phenylbutyl}benzenesulfonamide

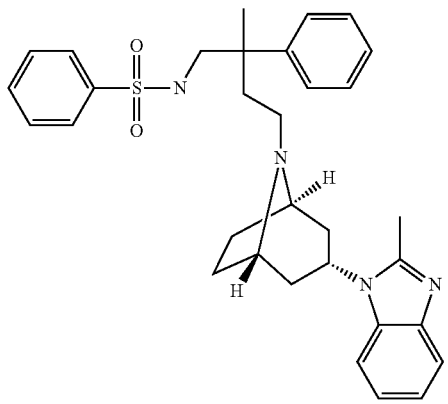 [SMILES: Cc1nc2ccccc2n1[C@H]1C[C@H]2CC[C@@H](C1)N2CCC(C)(CNS(=O)(=O)c1ccccc1)c1ccccc1]

To a solution of intermediate 23 (161 mg, 0.4 mmol) in CH$_2$Cl$_2$ (4 mL) was added diisopropylethylamine (0.175 mL, 1.0 mmol) followed by phenylsulfonyl chloride (0.065 mL, 0.5 mmol) and the solution stirred at room temperature under nitrogen atmosphere for 18 h. The reaction was concentrated in vacuo and purified by silica gel chromatography eluting with 0-5% methanol/CH$_2$Cl$_2$ to give the title compound (159 mg, 73%) as a white solid.

1H NMR (400 MHz, DMSO-d$_6$) d ppm 7.77 (d, J=6.97 Hz, 2H) 7.44-7.65 (m, 6H) 7.34 (d, 0H) 7.29 (d, J=4.40 Hz, 4H) 7.18 (d, J=4.22 Hz, 1H) 7.04-7.15 (m, 3H) 4.52 (br. s., 0H) 2.90 (d, J=6.60 Hz, 2H) 2.26-2.42 (m, 2H) 1.65-2.08 (m, 10H) 1.60 (br. s., 1H) 1.27 (s, 3H). HRMS: (M+H)$^+$ calcd for C$_{32}$H$_{38}$N$_4$O$_2$S+H, 543.2788. found, 543.2787.

Example 20

N-methyl-N-{2-methyl-4-[(1R,5S)-3-(2-methyl-1H-benzimidazol-1-yl)-8-azabicyclo[3.2.1]oct-8-yl]-2-phenylbutyl}benzenesulfonamide

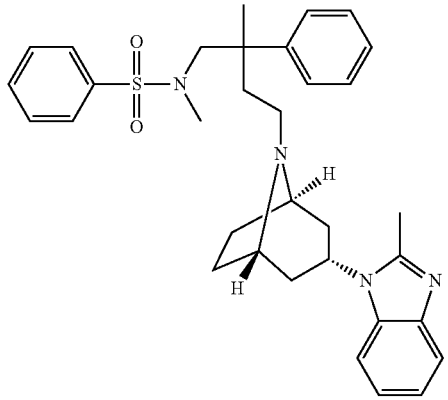 [SMILES: Cc1nc2ccccc2n1[C@H]1C[C@H]2CC[C@@H](C1)N2CCC(C)(CN(C)S(=O)(=O)c1ccccc1)c1ccccc1]

To a solution of the title compound from example 19 (65 mg, 0.12 mmol) in dry THF (2 mL) was added sodium hydride (6 mg, 0.14 mmol) as a 60% suspension in mineral oil and the solution stirred under a nitrogen atmosphere at room temperature for 30 min. Iodomethane (0.03 mL, 0.48 mmol) was added and the reaction stirred at room temperature for 1 h. An additional portion of iodomethane (0.02 mL, 0.32 mmol) was added and the solution stirred for 1 h more at room temperature. Water was added and the reaction partitioned between ethyl acetate and water. The organic layer was dried (MgSO$_4$) and concentrated in vacuo. The residue was purified by silica gel chromatography eluting with 0-4% methanol/CH$_2$Cl$_2$ to afford the title compound (50 mg, 75%) as a white solid.

1H NMR (400 MHz, DMSO-d$_6$) d ppm 7.71 (d, J=7.51 Hz, 2H) 7.61-7.68 (m, 1H) 7.58 (t, 2H) 7.46 (d, J=7.33 Hz, 1H) 7.24-7.41 (m, 5H) 7.17 (t, J=7.14 Hz, 1H) 7.01-7.13 (m, 2H) 4.41-4.59 (m, 1H) 3.38 (d, J=13.73 Hz, 1H) 2.93 (d, J=13.73 Hz, 1H) 2.33 (br. s., 2H) 2.03-2.14 (m, 2H) 2.00 (s, 3H) 1.86-1.96 (m, 1H) 1.64-1.84 (m, 7H) 1.47-1.62 (m, 2H) 1.38 (s, 3H). HRMS: (M+H)$^+$ calcd for C$_{33}$H$_{40}$N$_4$O$_2$S+H, 557.2945. found, 557.2944.

Preparation of Intermediate 23

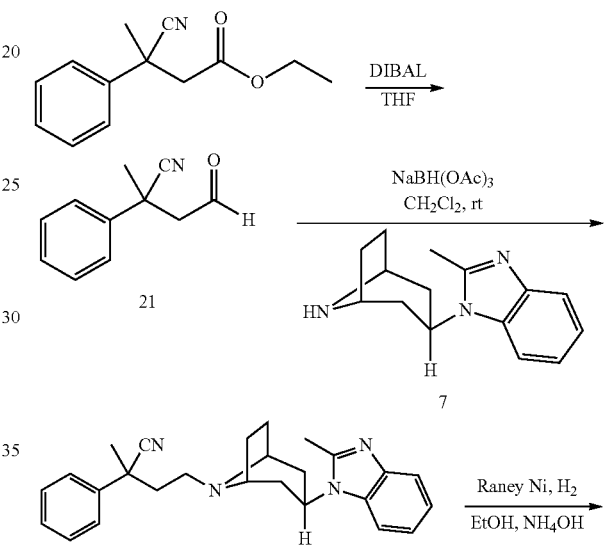

Intermediate 21

2-methyl-4-oxo-2-phenylbutanenitrile

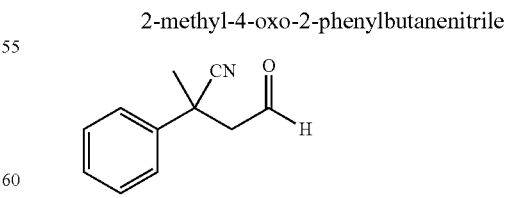

To a solution of ethyl 3-cyano-3-phenylbutanoate (1.0 g, 5.8 mmol) prepared as described in *Journal of Organic Chemistry*, vol. 19, pp. 1290-1295, in dry THF (10 mL) cooled to −78° C., was added DIBAL (2.1 mL) as a 1M solution in THF and stirred for 30 min whereupon the reaction was found to be incomplete. An additional portion of DIBAL (2.1 mL) was added and the reaction stirred for an additional 30 min. The reaction was poured into saturated NH$_4$Cl solution and extracted with ether. The organic layer was dried (MgSO$_4$) and concentrated in vacuo and the residue purified by silica gel chromatography eluting with 5-75% hexanes/ethyl acetate to afford intermediate 21 (190 mg, 19% yield) as an oil.

1H NMR (400 MHz, CHLOROFORM-d) d ppm 9.69 (s, 1H) 7.44-7.52 (m, 2H) 7.41 (t, J=7.70 Hz, 2H) 7.29-7.37 (m, 1H) 3.01 (dd, J=15.67, 1.92 Hz, 2H) 1.81 (s, 3H).

Intermediate 22

2-methyl-4-[3-(2-methyl-1H-benzimidazol-1-yl)-8-azabicyclo[3.2.1]oct-8-yl]-2-phenylbutanenitrile

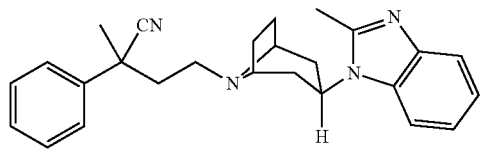 [SMILES: Cc1nc2ccccc2n1C1CC2CCC(C1)N2CCC(C)(C#N)c1ccccc1]

To a solution of 2-methyl-4-oxo-2-phenylbutanenitrile 21 (190 mg, 1.1 mmol) in CH$_2$Cl$_2$ (15 mL) was added 1-(8-azabicyclo[3.2.1]oct-3-yl)-2-methyl-1H-benzimidazole 7 (337 mg, 1.4 mmol) followed by NaBH(OAc)$_3$ (485 mg, 2.3 mmol) and the reaction stirred at room temperature for 18. The reaction was diluted with CH$_2$Cl$_2$ and washed with saturated NaHCO$_3$ solution. The organic layer was dried (MgSO$_4$) and concentrated in vacuo. The residue was purified by silica gel chromatography eluting with 10-50% hexanes/ethyl acetate to afford intermediate 22 (375 mg, 85% yield) as a white solid.

1H NMR (400 MHz, CHLOROFORM-d) d ppm 7.67 (d, J=7.33 Hz, 1H) 7.46-7.55 (m, 2H) 7.41 (t, J=7.42 Hz, 2H) 7.33 (d, J=7.33 Hz, 2H) 7.06-7.21 (m, 2H) 4.84 (br. s., 1H) 3.40 (br. s., 1H) 3.23 (br. s., 1H) 2.63 (s, 3H) 2.34-2.58 (m, 2H) 2.14-2.29 (m, 2H) 2.01-2.14 (m, 3H) 1.95 (t, J=12.36 Hz, 2H) 1.78 (s, 3H) 1.71 (d, J=7.69 Hz, 2H) 1.25 (t, J=7.05 Hz, 1H). ES-LCMS: 399.27 m/z (M+H)$^+$.

Intermediate 23

2-methyl-4-[(1R,5S)-3-(2-methyl-1H-benzimidazol-1-yl)-8-azabicyclo[3.2.1]oct-8-yl]-2-phenyl-1-butanamine

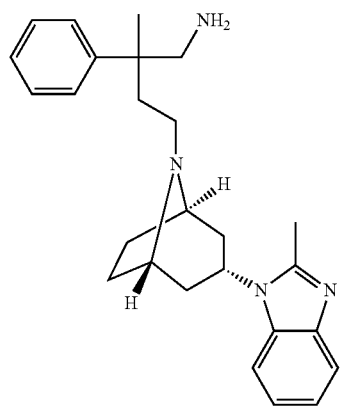 [SMILES: Cc1nc2ccccc2n1[C@H]1C[C@H]2CC[C@@H](C1)N2CCC(C)(CN)c1ccccc1]

To a solution of 2-methyl-4-[3-(2-methyl-1H-benzimidazol-1-yl)-8-azabicyclo[3.2.1]oct-8-yl]-2-phenylbutanenitrile 22 (375 mg, 0.94 mmol) in ethanol (15 mL) was added conc. NH$_4$OH (2 mL) followed by a spatula of Raney nickel and the solution heated to 50° C. under an atmosphere of 50 psi hydrogen for 18 h. The reaction was filtered through celite and concentrated in vacuo to afford intermediate 23 (350 mg, 90% yield) as a white solid.

1H NMR (400 MHz, CHLOROFORM-d) d ppm 7.64 (d, J=6.96 Hz, 1H) 7.26-7.43 (m, 5H) 7.06-7.22 (m, 3H) 4.55-4.84 (m, 1H) 3.27-3.46 (m, 2H) 2.94 (d, J=13.00 Hz, 1H) 2.75 (d, J=13.00 Hz, 1H) 2.57 (s, 3H) 2.32-2.50 (m, 2H) 2.11-2.26 (m, 1H) 1.83-2.11 (m, 6H) 1.47-1.83 (m, 5H) 1.33 (s, 3H). ES-LCMS: 403.35 m/z (M+H)$^+$.

Example 21

4,4-difluoro-N-{2-methyl-4-[(1R,5S)-3-(2-methyl-1H-benzimidazol-1-yl)-8-azabicyclo[3.2.1]oct-8-yl]-2-phenylbutyl}cyclohexanecarboxamide

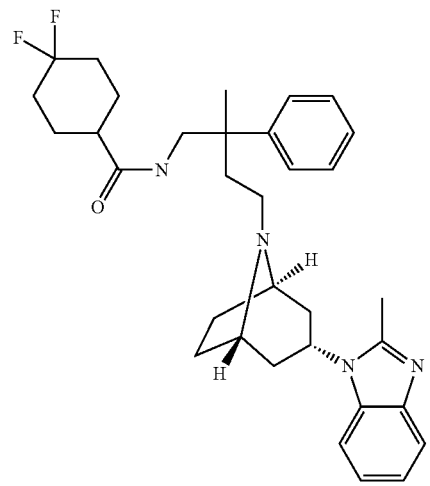 [SMILES: Cc1nc2ccccc2n1[C@H]1C[C@H]2CC[C@@H](C1)N2CCC(C)(CNC(=O)C1CCC(F)(F)CC1)c1ccccc1]

To a solution of 4,4-difluorocyclohexanecarboxylic acid (60 mg, 0.36 mmol) in CH$_2$Cl$_2$ (2 mL) was added HATU (140 mg, 0.36 mmol) followed by diisopropylethylamine (0.115 mL, 0.66 mmol) and the solution stirred at room temperature for 10 minutes under an atmosphere of nitrogen. A solution of intermediate 23 (131 mg, 0.33 mmol) in CH$_2$Cl$_2$ (3 mL) was added to the reaction and stirred at room temperature for 18 h. The reaction was concentrated and purified by silica gel chromatography eluting with 0-5% methanol/CH$_2$Cl$_2$ to give the title compound (131 mg, 72%) as a white solid.

1H NMR (400 MHz, DMSO-d$_6$) d ppm 7.59 (s, 1H) 7.47 (d, J=1.65 Hz, 1H) 7.24-7.40 (m, 6H) 7.18 (t, J=6.69 Hz, 1H) 7.04-7.15 (m, 2H) 4.55 (br. s., 1H) 2.21-2.42 (m, 4H) 1.39-2.12 (m, 16H) 1.26 (s, 3H). HRMS: (M+H)$^+$ calcd for C$_{33}$H$_{42}$F$_2$N$_4$O+H, 549.3399. found, 549.3401.

Example 22

4,4-difluoro-N-methyl-N-{2-methyl-4-[(1R,5S)-3-(2-methyl-1H-benzimidazol-1-yl)-8-azabicyclo[3.2.1]oct-8-yl]-2-phenylbutyl}cyclohexanecarboxamide

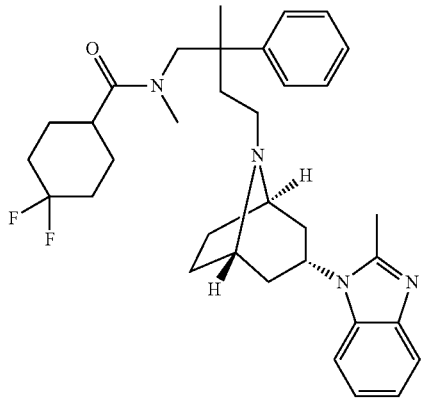 [SMILES: Cc1nc2ccccc2n1[C@H]1C[C@H]2CC[C@@H](C1)N2CCC(C)(CN(C)C(=O)C1CCC(F)(F)CC1)c1ccccc1]

To a solution of the title compound from example 21 (100 mg, 0.18 mmol) in dry DMF (1.5 mL) was added sodium hydride (9 mg, 0.22 mmol) as a 60% suspension in mineral oil and the solution stirred under a nitrogen atmosphere at room temperature for 30 min. Iodomethane (0.06 mL, 0.9 mmol) was added and the reaction stirred at room temperature for 2 h. Water was added and the reaction partitioned between ethyl acetate and water. The organic layer was dried (MgSO$_4$) and concentrated in vacuo. The residue was purified by silica gel chromatography eluting with 0-5% methanol/CH$_2$Cl$_2$ followed by purification by HPLC eluting with 5-70% water/acetonitrile/0.1% TFA to afford the title compound (9 mg, 7%) which was isolated as the trifluoroacetate salt.

1H NMR (500 MHz, CHLOROFORM-d) d ppm 7.94 (d, J=4.85 Hz, 1H) 7.49 (br. s., 4H) 7.32-7.44 (m, 4H) 7.29 (t, J=7.05 Hz, 1H) 5.73 (br. s., 1H) 4.07 (br. s., 2H) 3.91 (d, J=13.64 Hz, 1H) 3.37 (d, J=13.64 Hz, 1H) 3.06 (br. s., 2H) 2.89 (br. s., 3H) 2.68 (s, 3H) 2.57 (br. s., 4H) 2.26-2.43 (m, 5H) 2.08-2.26 (m, 5H) 1.83 (br. s., 4H) 1.66-1.76 (m, 1H) 1.38 (s, 3H). HRMS: (M+H)$^+$ calcd for C$_{34}$H$_{44}$F$_2$N$_4$O+H, 563.3556. found, 563.3557.

Example 23

4,4-difluoro-N-(2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)cyclohexanecarboxamide

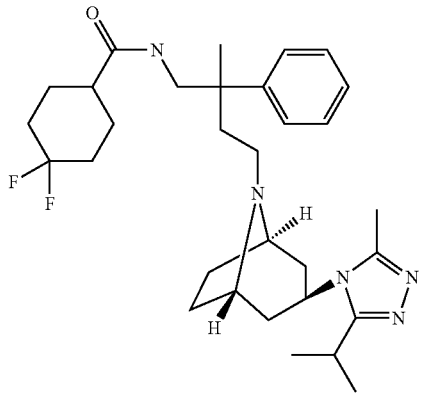 [SMILES: Cc1nnc(C(C)C)n1[C@@H]1C[C@H]2CC[C@@H](C1)N2CCC(C)(CNC(=O)C1CCC(F)(F)CC1)c1ccccc1]

The title compound was synthesized by coupling 4,4-difluorocyclohexanecarboxylic acid and (2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)amine (intermediate 24) as described in example 21.

1H NMR (400 MHz, METHANOL-d$_4$) d ppm 7.30-7.47 (m, 5H) 7.25 (t, J=6.50 Hz, 1H) 4.55-4.73 (m, 1H) 4.16 (br. s., 2H) 3.46-3.64 (m, 3H) 3.39 (d, J=13.55 Hz, 1H) 2.83-2.98 (m, 1H) 2.74 (s, 3H) 2.66 (t, J=13.28 Hz, 2H) 1.94-2.37 (m, 12H) 1.57-1.88 (m, 4H) 1.17-1.47 (m, 9H). HRMS: (M+H)$^+$ calcd for C$_{31}$H$_{45}$F$_2$N$_5$O+H, 542.3665. found, 542.3669.

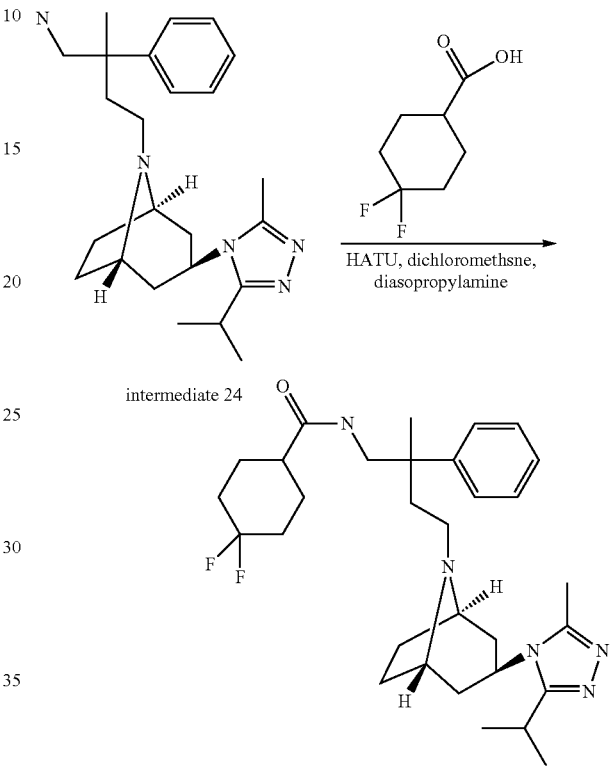

The synthesis of the intermediate 24 was accomplished from ethyl 3-cyano-3-phenylbutanoate (described e.g. in Synthetic Communications (1993), 23(10), 1371-7) by similar route one described for intermediate 6

Example 24

N-(2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)benzenesulfonamide

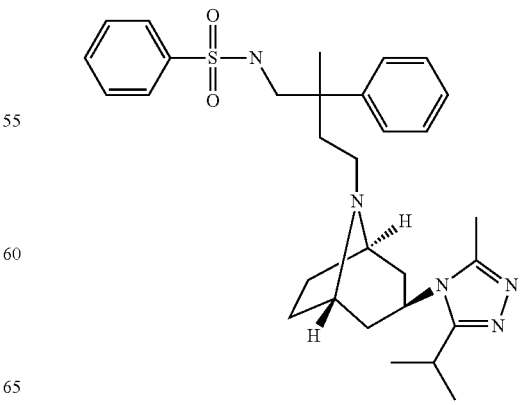

To a solution of intermediate 24 (158 mg, 0.4 mmol) in CH$_2$Cl$_2$ (4 mL) was added diisopropylethylamine (0.175 mL, 1.0 mmol) followed by phenylsulfonyl chloride (0.065 mL, 0.5 mmol) and the solution stirred at room temperature under nitrogen atmosphere for 18 h. The reaction was concentrated in vacuo and purified by silica gel chromatography eluting with 0-5% methanol/CH$_2$Cl$_2$ to give the title compound (150 mg, 70%) as a white solid.
Isolated as the Trifluoroacetate Salt.
1H NMR (400 MHz, METHANOL-d$_4$) d ppm 7.84 (d, J=7.69 Hz, 2H) 7.49-7.67 (m, 4H) 7.27-7.39 (m, 4H) 7.24 (br. s., 1H) 4.57-4.75 (m, 1H) 4.20 (d, J=15.75 Hz, 2H) 3.42-3.61 (m, 1H) 3.16 (d, J=13.19 Hz, 1H) 2.98 (d, J=13.19 Hz, 1H) 2.89 (br. s., 2H) 2.72 (br. s., 3H) 2.65 (t, J=13.37 Hz, 2H) 2.19-2.41 (m, 5H) 2.06-2.24 (m, 3H) 1.22-1.52 (m, 9H). HRMS: (M+H)$^+$ calcd for C$_{30}$H$_{41}$N$_5$O$_2$S+H, 536.3054. found, 536.3054.

Example 25

Biological Activity

HOS Assay

HOS-Luc cells were created by introducing an HIV-1 LTR-luciferase reporter into HOS-CD4.CCR5 (NIH AIDS Research and Reference Reagents Program, cat. #3318). The cells were propagated in DMEM complete medium. Cells were split 1:20 by standard trypsinization when confluency reached 80% (roughly every 2 to 3 days).

Black-walled 96-well tissue culture plates were seeded with HOS-Luc at 6×10$^3$ cells per well in 50 µL DMEM containing 2% FBS and placed in a humidified incubator at 37° C., 5% CO$_2$ overnight. The following day, test compounds were serially diluted in 4-fold increments at 2× the final concentration in DMEM+2% FBS+0.2% DMSO. Diluted compound (50 µL) was transferred to the HOS-Luc cells and the plates were placed in a humidified incubator at 37° C., 5% CO$_2$ for 1 hr. An additional 60 µL of 2× compound was transferred to a clear-walled 96-well tissue culture plate and 60 µL of virus (diluted 1:50 in tissue culture media) was added to each well and thoroughly mixed. The virus input was previously determined by titrating the virus under assay conditions without compound and selecting a dilution that gives a response in the linear range of the curve and a signal to background of at least 30. The HIV/compound mixture (100 µL) was transferred to the black-walled plates containing 100 µL of cells/compound. The plates were placed in a humidified incubator at 37° C., 5% CO$_2$ for four days. Following the four-day incubation, 150 µL of supernatant was removed and 50 µL of reconstituted Luclite (Promega) was added to each well. For cytotoxicity assessment, 50 µL of reconstituted CellTiter-GLo (Promega) was added to each well. Each plate was topsealed and read in a Topcount (Packard) luminometer at 1 s/well.

Raw data from the HOS-Luc assay were expressed as Relative Light Units (RLU) and normalized according to the following formula:

(RLU at drug [ ]/RLU no drug)*100=% control

The potency of test compounds are reported as IC50 values derived from the four parameter Hill equation, defined as:

$$y=V\max*(1-(x^n/(K^n+x^n)))+Y2$$

Where:
x=Log$_{10}$ [compound]
y=normalized response data
V$_{max}$=upper bound of response
K=IC$_{50}$
Y$_2$=lower bound or baseline of response
n=hill coefficient
Compounds of Formula (I) have IC$_{50}$ values:

| Example | HOS IC$_{50}$ [µM] |
|---------|--------------------|
| 1       | **                 |
| 2       | ***                |
| 3       | **                 |
| 4       | **                 |
| 5       | **                 |
| 6       | **                 |
| 7       | **                 |
| 8       | **                 |
| 9       | **                 |
| 10      | **                 |
| 11      | **                 |
| 12      | **                 |
| 13      | ***                |
| 14      | **                 |
| 15      | **                 |
| 16      | *                  |
| 17      | *                  |
| 18      | *                  |
| 19      | *                  |
| 20      | ***                |
| 21      | *                  |
| 22      | *                  |
| 23      | *                  |
| 24      | *                  |

* 1-0.1 µM
** 0.1-0.01 µM
*** <0.01 µM

The invention claimed is:
1. A compound of Formula (I):

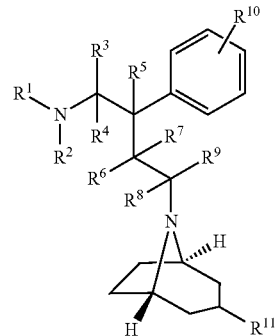

(I)

wherein:
R$^1$ is
(a) S(O)$_2$R$^{12}$ wherein R$^{12}$ is C$_{1-6}$alkyl; haloalkyl; heterocyclyl optionally substituted with oxo; aryl optionally substituted with CN or C(O)N(R$^{13}$)$_2$ wherein R$^{13}$ is hydrogen; or NR$^{14}$ wherein R$^{14}$ is C$_{3-6}$cycloalkyl optionally substituted with one or more halogen;
(b) P(O)(OR$^{15}$)$_2$ wherein R$^{15}$ is C$_{1-6}$alkyl; or
(c) C(O)R$^{14}$;
R$^2$ is hydrogen or C$_{1-6}$alkyl;
R$^3$-R$^9$ is hydrogen, halogen or C$_{1-6}$alkyl;
R$^{10}$ is one or more substituents independently selected from the group consisting of hydrogen, halogen and C$_{1-6}$alkyl;
R$^{11}$ is heterocyclyl optionally substituted with one or more substituents independently selected from the group consisting of C$_{1-6}$alkyl and C(O)R$^{15}$;

or a pharmaceutically acceptable salt thereof.

2. A compound of Formula (Ia)

(Ia)

wherein:
$R^1$ is
  (a) $S(O)_2R^{12}$ wherein $R^{12}$ is $C_{1-6}$alkyl; haloalkyl; heterocyclyl optionally substituted with oxo; aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen;
  (b) $P(O)(OR^{15})_2$ wherein $R^{15}$ is $C_{1-6}$alkyl; or
  (c) $C(O)R^{14}$;
$R^2$ is hydrogen or $C_{1-6}$alkyl;
$R^3$-$R^9$ is hydrogen, halogen or $C_{1-6}$alkyl;
or a pharmaceutically acceptable salt thereof.

3. A compound of Formula (I) according to claim 1 wherein:
$R^1$ is
  (a) $S(O)_2R^{12}$ wherein $R^{12}$ is $C_{1-6}$alkyl; haloalkyl; heterocyclyl optionally substituted with oxo; aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen; or
  (b) $P(O)(OR^{15})_2$ wherein $R^{15}$ is $C_{1-6}$alkyl;
$R^2$ is hydrogen or $C_{1-6}$alkyl;
$R^3$-$R^9$ is hydrogen;
$R^{10}$ is hydrogen;
$R^{11}$ is heterocyclyl optionally substituted with one or more substituents independently selected from the group consisting of $C_{1-6}$alkyl and $C(O)R^{15}$;
or a pharmaceutically acceptable salt thereof.

4. A compound of Formula (I) according to claim 1 wherein:
$R^1$ is
  (a) $S(O)_2R^{12}$ wherein $R^{12}$ is aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen;
$R^2$ is hydrogen or $C_{1-6}$alkyl;
$R^3$-$R^9$ is hydrogen;
$R^{10}$ is hydrogen;
$R^{11}$ is heterocyclyl optionally substituted with one or more substituents independently selected from the group consisting of $C_{1-6}$alkyl and $C(O)R^{15}$;
or a pharmaceutically acceptable salt thereof.

5. A compound of Formula (Ia) according to claim 2 wherein:
$R^1$ is
  (a) $S(O)_2R^{12}$ wherein $R^{12}$ is $C_{1-6}$alkyl; haloalkyl; heterocyclyl optionally substituted with oxo; aryl optionally substituted with CN or $C(O)N(R^{13})_2$ wherein $R^{13}$ is hydrogen; or $NR^{14}$ wherein $R^{14}$ is $C_{3-6}$ cycloalkyl optionally substituted with one or more halogen; or
  (b) $P(O)(OR^{15})_2$ wherein $R^{15}$ is $C_{1-6}$alkyl;
$R^2$ is hydrogen or $C_{1-6}$alkyl;
$R^3$-$R^9$ is hydrogen;
or a pharmaceutically acceptable salt thereof.

6. A compound of Formula (Ia) according to claim 2 wherein:
$R^1$ is
  (a) $S(O)_2R^{12}$ wherein $R^{12}$ is aryl optionally substituted with CN or $C(O)N(R^{13})_2$ wherein $R^{13}$ is hydrogen; or $NR^{14}$ wherein $R^{14}$ is $C_{3-6}$cycloalkyl optionally substituted with one or more halogen;
$R^2$ is hydrogen or $C_{1-6}$alkyl;
$R^3$-$R^9$ is hydrogen;
or a pharmaceutically acceptable salt thereof.

7. A compound of according to claim 1 wherein $R^{11}$ is benzimidazolyl or triazolyl.

8. A compound selected from the group consisting of:
N-{4-[(1R,5S)-3-(2-methyl-1H-benzimidazol-1-yl)-8-azabicyclo[3.2.1]oct-8-yl]-2-phenylbutyl};
N-methyl-N-{4-[(1R,5S)-3-(2-methyl-1H-benzimidazol-1-yl)-8-azabicyclo[3.2.1]oct-8-yl]-2-phenylbutyl}benzenesulfonamide;
3-cyano-N-{4-[(1R,5S)-3-(2-methyl-1H-benzimidazol-1-yl)-8-azabicyclo[3.2.1]oct-8-yl]-2-phenylbutyl}benzenesulfonamide;
4-cyano-N-{4-[(1R,5S)-3-(2-methyl-1H-benzimidazol-1-yl)-8-azabicyclo[3.2.1]oct-8-yl]-2-phenylbutyl}benzenesulfonamide;
N-{4-[(1R,5S)-3-(2-methyl-1H-benzimidazol-1-yl)-8-azabicyclo[3.2.1]oct-8-yl]-2-phenylbutyl}methanesulfonamide;
3-[({4-[(1R,5S)-3-(2-methyl-1H-benzimidazol-1-yl)-8-azabicyclo[3.2.1]oct-8-yl]-2-phenylbutyl}amino)sulfonyl]benzamide;
N-{4-[(1R,5S)-3-(2-methyl-1H-benzimidazol-1-yl)-8-azabicyclo[3.2.1]oct-8-yl]-2-phenylbutyl}-2-oxo-2,3-dihydro-1,3-benzoxazole-6-sulfonamide;
4-[({4-[(1R,5S)-3-(2-methyl-1H-benzimidazol-1-yl)-8-azabicyclo[3.2.1]oct-8-yl]-2-phenylbutyl}amino)sulfonyl]benzamide;
dimethyl {4-[(1R,5S)-3-(2-methyl-1H-benzimidazol-1-yl)-8-azabicyclo[3.2.1]oct-8-yl]-2-phenylbutyl}amidophosphate;
2,2,2-trifluoro-N-{4-[(1R,5S)-3-(2-methyl-1H-benzimidazol-1-yl)-8-azabicyclo[3.2.1]oct-8-yl]-2-phenylbutyl}ethanesulfonamide;
N-{4-[(1R,5S)-3-(2-methyl-3H-imidazo[4,5-c]pyridin-3-yl)-8-azabicyclo[3.2.1]oct-8-yl]-2-phenylbutyl}benzenesulfonamide;
N-{4-[(1R,5S)-3-(2-methyl-1H-benzimidazol-1-yl)-8-azabicyclo[3.2.1]oct-8-yl]-2-phenylbutyl}-4-morpholinesulfonamide;
N-{4-[(1R,5S)-3-(5-acetyl-2-methyl-4,5,6,7-tetrahydro-3H-imidazo[4,5-c]pyridin-3-yl)-8-azabicyclo[3.2.1]oct-8-yl]-2-phenylbutyl}benzenesulfonamide;
N-cyclobutyl-N'-{4-[(1R,5S)-3-(2-methyl-1H-benzimidazol-1-yl)-8-azabicyclo[3.2.1]oct-8-yl]-2-phenylbutyl}sulfamide;
N-(4,4-difluorocyclohexyl)-N'-{4-[(1R,5S)-3-(2-methyl-1H-benzimidazol-1-yl)-8-azabicyclo[3.2.1]oct-8-yl]-2-phenylbutyl}sulfamide;
4,4-difluoro-N-(4-{(1R,5S)-3-[3-methyl-5-(1-methylethyl)-4H-1,2,4-triazol-4-yl]-8-azabicyclo[3.2.1]oct-8-yl}-2-phenylbutyl)cyclohexanecarboxamide;

N-(4-{(1R,5S)-3-[3-methyl-5-(1-methylethyl)-4H-1,2,4-triazol-4-yl]-8-azabicyclo[3.2.1]oct-8-yl}-2-phenylbutyl)benzenesulfonamide;

3,3-difluoro-N-(4-{(1R,5S)-3-[3-methyl-5-(1-methylethyl)-4H-1,2,4-triazol-4-yl]-8-azabicyclo[3.2.1]oct-8-yl}-2-phenylbutyl)cyclobutanecarboxamide;

N-{2-methyl-4-[(1R,5S)-3-(2-methyl-1H-benzimidazol-1-yl)-8-azabicyclo[3.2.1]oct-8-yl]-2-phenylbutyl}benzenesulfonamide;

N-methyl-N-{2-methyl-4-[(1R,5S)-3-(2-methyl-1H-benzimidazol-1-yl)-8-azabicyclo[3.2.1]oct-8-yl]-2-phenylbutyl}benzenesulfonamide;

4,4-difluoro-N-{2-methyl-4-[(1R,5S)-3-(2-methyl-1H-benzimidazol-1-yl)-8-azabicyclo[3.2.1]oct-8-yl]-2-phenylbutyl}cyclohexanecarboxamide;

4,4-difluoro-N-methyl-N-{2-methyl-4-[(1R,5S)-3-(2-methyl-1H-benzimidazol-1-yl)-8-azabicyclo[3.2.1]oct-8-yl]-2-phenylbutyl}cyclohexanecarboxamide;

4,4-difluoro-N-(2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)cyclohexanecarboxamide;

N-(2-methyl-4-{(1R,5S)-3-[3-methyl-5-(1-methylethyl)-4H-1,2,4-triazol-4-yl]-8-azabicyclo[3.2.1]oct-8-yl}-2-phenylbutyl)benzenesulfonamide;

N-methyl-N-{(2S)-2-methyl-4-[(1R,5S)-3-(2-methyl-1H-benzimidazol-1-yl)-8-azabicyclo[3.2.1]oct-8-yl]-2-phenylbutyl}benzenesulfonamide; and pharmaceutically acceptable salts thereof.

9. A method of treatment of a HIV infection in a human comprising administering to said human an effective amount of a compound according to claim 1.

10. A pharmaceutical composition comprising a pharmaceutically effective amount of a compound according to claim 1 together with a pharmaceutically acceptable carrier.

* * * * *

UNITED STATES PATENT AND TRADEMARK OFFICE
CERTIFICATE OF CORRECTION

PATENT NO. : 8,592,395 B2
APPLICATION NO. : 13/386731
DATED : November 26, 2013
INVENTOR(S) : Maosheng Duan, Wieslaw Mieczyslaw Kazmierski and Matthew Tallant It is certified that error appears in the above-identified patent and that said Letters Patent is hereby corrected as shown below:

On Title Page 1, (56) References Cited:

The following references have been omitted and should be included:

Under 'FOREIGN PATENT DOCUMENTS'

"WO 2011/116287 A1  9/2011"

Under 'OTHER PUBLICATIONS'

"European Search Report EP10802932 dated March 6, 2013"

"Tallant, et al., Synthesis and evaluation of 2-phenyl-1,4-butanediamine-based CCR5 antagonists for the treatment of HIV-1" Bioorganic & Medicinal Chemistry Letters; 2011; pp. 1394-1398; Vol. 21 (5); Elsevier Science; GB"

Signed and Sealed this
Third Day of February, 2015

Michelle K. Lee
*Deputy Director of the United States Patent and Trademark Office*